US007883508B2

(12) United States Patent
Thao et al.

(10) Patent No.: US 7,883,508 B2
(45) Date of Patent: Feb. 8, 2011

(54) CONTACT-SENSITIVE PRESSURE-SENSITIVE CONDUCTIVE COMPOSITE ELECTRODE AND METHOD FOR ABLATION

(75) Inventors: Chou Thao, Brooklyn Park, MN (US); Saurav Paul, Minnetonka, MN (US); Kedar Ravindra Belhe, Minnetonka, MN (US); Hong Cao, Savage, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1075 days.

(21) Appl. No.: 11/647,294

(22) Filed: Dec. 29, 2006

(65) Prior Publication Data

US 2008/0161789 A1 Jul. 3, 2008

(51) Int. Cl.
*A61B 18/18* (2006.01)

(52) U.S. Cl. ............................. 606/40; 606/49; 606/32

(58) Field of Classification Search ............. 606/32–49
See application file for complete search history.

(56) References Cited

U.S. PATENT DOCUMENTS 4,911,174 A 3/1990 Pederson et al.
5,028,394 A 7/1991 Lowell, Jr. et al.
5,341,807 A 8/1994 Nardella
5,372,603 A 12/1994 Acker et al.
5,382,247 A 1/1995 Cimino et al.
5,447,539 A 9/1995 Kelly et al.
5,472,441 A 12/1995 Edwards et al.
5,545,161 A 8/1996 Imran
5,685,878 A 11/1997 Falwell et al.
5,697,925 A 12/1997 Taylor
5,836,990 A 11/1998 Li
5,868,737 A 2/1999 Taylor et al.
5,913,854 A 6/1999 Maguire et al.
5,947,905 A 9/1999 Hadjicostis et al.

(Continued)

FOREIGN PATENT DOCUMENTS

EP 1491139 12/2004

(Continued)

OTHER PUBLICATIONS

Biopac Systems, Inc., "Micro Pressure Measurement System—Product Overview," 39 pages, 2000.

(Continued)

*Primary Examiner*—Thomas J Sweet
*Assistant Examiner*—Amanda Scott
(74) *Attorney, Agent, or Firm*—Wiley Rein LLP

(57) ABSTRACT

A catheter assembly for pressure-sensitive control of ablation treatment is disclosed. The assembly includes a conductive element, an electrode, and a pressure sensitive conductive composite member positioned between the conductive element and the electrode. At least one of the conductive pin, the pressure sensitive conductive composite element and the ablation electrode are moveable to create an engagement position and a non-engagement position. In the engagement position, the elements are electrically coupled such that ablation energy may be delivered from the conductive pin to the ablation electrode via the pressure sensitive conductive composite element. In the non-engagement position, the elements are electrically decoupled such that ablation energy is not delivered to the ablation electrode. A related method for pressure-sensitive control of ablation is also disclosed.

18 Claims, 17 Drawing Sheets

U.S. PATENT DOCUMENTS

| | | | |
|---|---|---|---|
| 6,013,074 | A | 1/2000 | Taylor |
| 6,039,731 | A | 3/2000 | Taylor et al. |
| 6,066,139 | A | 5/2000 | Ryan et al. |
| 6,113,592 | A | 9/2000 | Taylor |
| 6,113,593 | A | 9/2000 | Tu et al. |
| 6,171,304 | B1 | 1/2001 | Netherly et al. |
| 6,210,406 | B1 | 4/2001 | Webster |
| 6,217,573 | B1 | 4/2001 | Webster |
| 6,217,574 | B1 | 4/2001 | Webster |
| 6,221,023 | B1 | 4/2001 | Matsuba et al. |
| 6,246,898 | B1 | 6/2001 | Vesely et al. |
| 6,264,653 | B1 | 7/2001 | Falwell |
| 6,272,371 | B1 | 8/2001 | Shlomo |
| 6,291,568 | B1 | 9/2001 | Lussey et al. |
| 6,304,776 | B1 | 10/2001 | Muntermann |
| 6,322,558 | B1 | 11/2001 | Taylor et al. |
| 6,325,799 | B1 | 12/2001 | Goble |
| 6,391,024 | B1 | 5/2002 | Sun et al. |
| 6,423,057 | B1 | 7/2002 | He et al. |
| 6,495,069 | B1 | 12/2002 | Lussey et al. |
| 6,616,657 | B2 | 9/2003 | Simpson et al. |
| 6,620,159 | B2 | 9/2003 | Hegde |
| 6,638,222 | B2 | 10/2003 | Chandrasekaran et al. |
| 6,646,540 | B1 | 11/2003 | Lussey |
| 6,696,844 | B2 | 2/2004 | Wong et al. |
| 6,730,082 | B2 | 5/2004 | Messing et al. |
| 6,845,264 | B1 | 1/2005 | Skladnev et al. |
| 6,882,885 | B2 | 4/2005 | Levy, Jr. et al. |
| 6,936,047 | B2 | 8/2005 | Nasab et al. |
| 6,974,457 | B2 | 12/2005 | Gibson |
| 6,999,821 | B2 | 2/2006 | Jenney et al. |
| 7,060,965 | B2 | 6/2006 | Vidovic et al. |
| 2002/0123749 | A1 | 9/2002 | Jain |
| 2003/0204184 | A1 | 10/2003 | Ferek-Patric |
| 2004/0039298 | A1 | 2/2004 | Abreu |
| 2004/0133092 | A1 | 7/2004 | Kain |
| 2004/0133166 | A1 | 7/2004 | Moberg et al. |
| 2005/0049583 | A1 | 3/2005 | Swanson et al. |
| 2005/0119650 | A1 | 6/2005 | Sanders et al. |
| 2005/0137662 | A1 | 6/2005 | Morris et al. |
| 2005/0159739 | A1 | 7/2005 | Paul et al. |
| 2005/0267332 | A1 | 12/2005 | Paul et al. |
| 2005/0267458 | A1 | 12/2005 | Paul et al. |
| 2005/0267467 | A1 | 12/2005 | Paul et al. |
| 2006/0095022 | A1 | 5/2006 | Moll et al. |
| 2006/0111706 | A1 | 5/2006 | Truckai et al. |
| 2006/0137464 | A1 | 6/2006 | Baudendistel |
| 2006/0249705 | A1 | 11/2006 | Wang et al. |
| 2006/0264831 | A1 | 11/2006 | Skwarek et al. |
| 2006/0278248 | A1 | 12/2006 | Viswanathan |

FOREIGN PATENT DOCUMENTS

| | | |
|---|---|---|
| WO | 2005039835 | 5/2005 |

OTHER PUBLICATIONS

"Fiber Optic Interferometer Fabry-Perot," available from http://physics.nad.ru/Physics/English/ifp_txt.htm at least as early as Oct. 15, 2007, 4 pages.

Medical Product Manufacturing News "Need to Know," 1 page, Sep. 2007.

BIOSEB: Samba—Blood Pressure System, available from http://www.bioseb.com/anglais/default/item_id=904_cat_id=3+Samba%20-%20Blood%20Pressure%System.php at least as early as Oct. 15, 2007, 3 pages.

Samba Sensors, "The Samba Technology," available from http://www.samba.se/index2.cfm?PageID=45 at least as early as Oct. 15, 2007, 1 page.

Samba Sensors, "Publications related to Samba Sensors AB," 3 pages.

PCT International Seach Report and Written Opinion of the International Seaching Authority for PCT/US06/39881 dated Jun. 30, 2008, 4 pages.

PCT International Search Report and Written Opinion of the International Searching Authority for PCT/US07/80981 dated Apr. 16, 2008, 6 pages.

PCT International Search Report and Written Opinion of the International Searching Authority for PCT/US07/80983 dated Apr. 2, 2008, 5 pages.

PCT International Search Report and Written Opinion of the International Searching Authority for PCT/US06/42119 dated Sep. 13, 2007, 5 pages.

International Search Report and Written Opinion of the International Searching Authority for PCT/US07/88680 dated Jul. 2, 2008.

Ghosh et al. Development of Layered Functional Fiber Based Micro-Tubes. National Textile Center Annual Report: Nov. 2005. Retrieved from the Internet on Jun. 24, 2008: <http://www.ntcresearch.org/pdf-rpts/AnRp05/F02-NS05-A5.pdf>.

NuSil R-2637 Product Profile Dec. 12, 2006.

International Search Report and Written Opinion of the International Searching Authority for PCT/US07/88723 dated Jul. 7, 2008.

International Search Report of the International Searching Authority for PCT/US07/89099 dated Jul. 7, 2008.

International Search Report and Written Opinion of the International Searching Authority for PCT/US07/88729 dated May 16, 2008.

Peratech Ltd. (website page), QTC Pills, Retrofittable Components for Improved Switching Performance, Jan. 2004, www.peratech.co.uk.

CONTACT-SENSITIVE PRESSURE-SENSITIVE CONDUCTIVE COMPOSITE ELECTRODE AND METHOD FOR ABLATION

CROSS-REFERENCE TO RELATED APPLICATIONS

This application is related to U.S. application Ser. Nos. 11/647,316 filed 29 Dec. 2006 (entitled "Pressure-Sensitive Conductive Composite Electrode and Method for Ablation"); Ser. No. 11/647,314 filed 29 Dec. 2006 (entitled "Pressure-Sensitive Conductive Composite Contact Sensor and Method for Contact Sensing"); ser. No. 11/647,279 filed 29 Dec. 2006 (entitled "Design of Ablation Electrode with Tactile Sensor") all of which are hereby incorporated by reference as though fully set forth herein.

BACKGROUND OF THE INVENTION a. Field of the Invention

The present invention pertains generally to an electrophysiological device and method for providing energy to biological tissue and, more particularly, to an ablation apparatus with greater contact sensitivity.

b. Background Art

Ablation devices, including radio frequency ("RF") ablation devices, have heretofore been provided, but not using a pressure sensitive conductive composite ("PSCC") based electrodes (including, for example, quantum tunneling composites ("QTC") and other pressure-sensitive, conductive polymers).

Many medical procedures, including for example, creating lesions with electrical energy, rely on good contact between the medical device and the tissue. In some catheter applications, the point of electrode-tissue contact is typically 150 cm away from the point of application of force. This gives rise to functional and theoretical challenges associated with conventional devices, and thus, the ability to accurately assess tissue contact is increasingly important, especially in connection with ablation treatment.

There is a need for improved ablation devices that provide greater contact sensitivity for control of ablation treatments using electrical energy.

There is a need for improved ablation devices that provide greater contact sensitivity for RF ablation treatments.

There is also a need for improved ablation devices that better concentrate the RF energy to the region of tissue that is in contact with the electrode.

BRIEF SUMMARY OF THE INVENTION

Disclosed herein is an electrode assembly having a conductive pin for conducting ablation energy; an ablation electrode at a distal end of the electrode assembly; and pressure sensitive conductive composite element disposed between the conductive pin and the ablation electrode. The pressure sensitive conductive composite element is positioned such that when it is compressed between the conductive pin and the ablation electrode, the pressure sensitive conductive composite element conducts ablation energy from the conductive pin to the ablation electrode. The electrode assembly may also contain a first shaft in which the ablation electrode is disposed at a distal end; a second shaft in which the conductive pin is disposed; and a spring that permits the first and second shafts to be compressed toward each other. Optionally, collars or anchors may be established on each of the first and second shafts such that the spring may be anchored between the two collars during compression.

Also disclosed is a catheter assembly for conducting ablative energy having a catheter body with an ablation electrode; a pressure sensitive conductive composite member; a conductive pin for conducting ablation energy; and a spring that is capable of being in at least a first state and a second state. The first state is one in which the spring electrically decouples the electrode from at least one of the conductive pin and the pressure sensitive conductive composite member. The spring is also compressible into a second state wherein pressure is applied to the pressure sensitive conductive composite member to place it in a conductive state, thereby transferring ablation energy from the conductive pin to the ablation electrode. Optionally, one or more pressure transfer members may be disposed between the pressure sensitive conductive composite member and the ablation electrode. Ideally, the pressure transfer members are disposed such that pressure applied to the ablation electrode is transferred through the at least one pressure transfer member to the pressure sensitive conductive composite member.

Also disclosed is a method of treating tissue. An electrode assembly is provided having a conductive element for conducting RF energy and an ablation electrode at a distal end of the electrode assembly. A pressure sensitive conductive composite member is disposed between the conductive element and the ablation electrode. The electrode assembly may be positioned in contact with a tissue to be treated, and the operator exerts sufficient force upon the tissue through the electrode assembly such that the pressure sensitive conductive composite member becomes conductive and permits the delivery of RF energy to the tissue. Preferably, the ablation assembly is configured such that at least two of the conductive element, the ablation electrode and the pressure sensitive conductive composite element may be in an electrically decoupled state, but after moving at least one of the conductive element, the ablation electrode and the pressure sensitive conductive composite element, the elements are electrically coupled such that ablation energy may be delivered from the conductive pin to the ablation electrode via the pressure sensitive conductive composite element. Optionally, control signals may be used to control the RF generator that provides the RF ablation energy. For example, if the degree of contact is assessed such that it is determined that there is an insufficient degree of contact, the RF generator may be disabled to preclude ablation. Alternatively, the tissue/electrode interface may be monitored for commencement of the delivery of ablation energy, and then, a timer may be executed such that the RF generator is disabled after having generated RF energy for a fixed time period.

An electrode assembly is also disclosed having a conductive pin for conducting ablation energy; an ablation electrode at a distal end of the electrode assembly; a pressure sensitive conductive composite element disposed between the conductive pin and the ablation electrode; and an engagement assembly. The engagement assembly moves at least one of the conductive pin, the pressure sensitive conductive composite element and the ablation electrode to create an engagement position and a non-engagement position. The engagement position electrically couples the conductive pin, the pressure sensitive conductive composite element and the ablation electrode, such that ablation energy may be delivered from the conductive pin to the ablation electrode via the pressure sensitive conductive composite element. The non-engagement position electrically decouples at least two of the conductive pin, the pressure sensitive conductive composite element, and the ablation electrode, such that ablation energy is not delivered to the ablation electrode. The engagement assembly may comprise: a first shaft in which the ablation electrode is disposed at a distal end; a second shaft in which the conductive pin is disposed; and a spring that permits the first and second shafts to be compressed toward each other.

Each of the embodiments of the present invention utilizes a pressure sensitive conductive composite medium. Of course, the pressure sensitive conductive composite element may also comprise a quantum tunneling composite material.

An objective of the present invention is to provide a PSCC electrode that may be used for RF ablation treatment.

Another object of the present invention is to provide a method of manufacturing an electrode assembly for ablation therapy.

Another object of the present invention is to provide a flexible, pressure-sensitive, conductive polymer-based electrode for RF ablation, which can be used in a wide variety of tissue environments.

Yet another object of the invention is to provide an ablation electrode that better concentrates the energy to the region of tissue that is in contact with the electrode.

Yet another object of the invention is to provide an ablation electrode that mitigates edge-effects, hot spots and coagulum formation during the ablation process.

A further object of the invention is to provide a system for RF ablation treatment, including an RF generator and a coolant supply system that can be connected to a pressure-sensitive, conductive polymer-based electrode to provide control over the RF ablation process.

Another object of the present invention is to provide an electrode with a contact sensor assembly that can sense contact with tissue based on the pressure that is exerted on the sensor, and then use the contact information for medical treatments (such as ablation).

Another object of the present invention is to provide an ablation electrode with contact sensor that measures pressure that is being exerted on the sensor based on direct or indirect contact between the sensor and another mass, such as tissue.

Yet another object of the present invention is to provide a method of ablation using contact sensing.

Still another object of the present invention is to provide a inexpensive, flexible, contact sensitive electrode for dry surface applications.

Another object is to improve the efficiency, safety and efficacy of dry RF ablation devices.

Another object is to prevent arcing during dry RF ablation treatments.

Yet another object of the present invention is to provide a method of manufacturing an electrode having a pressure-sensitive, conductive polymer-based contact sensor.

Yet another objective of this invention is to provide a method for RF ablation that utilizes a pressure-sensitive, conductive polymer-based electrode in accordance with the teachings herein.

Another objective of the present invention is to provide a PSCC-based sensor that may be used in connection with RF ablation treatment.

An advantage of using a PSCC in ablation applications is that the PSCC mitigates arcing.

Another advantage of using a PSCC in an ablation device is that the design may be significantly less complicated, which permits reduced manufacturing costs and increased reliability.

The foregoing and other aspects, features, details, utilities, and advantages of the present invention will be apparent from reading the following description and claims, and from reviewing the accompanying drawings.

DETAILED DESCRIPTION OF THE INVENTION

Figure 1A:
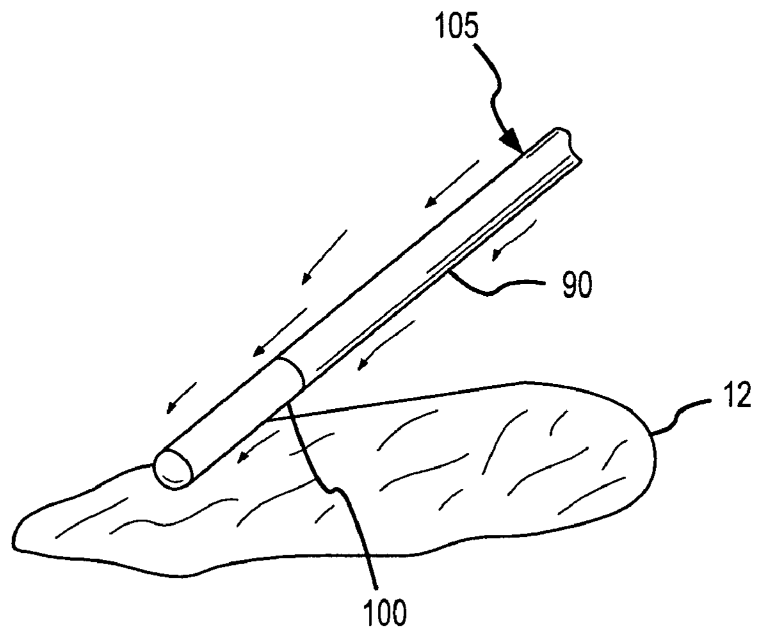
FIGS. 1A and 1B are perspective views of a sample embodiment of the present invention, illustrating how the present invention may be used to assess contact with tissue and ablate tissue.

A contact-sensitive PSCC electrode for ablation is disclosed, along with methods for using and methods of manufacturing the PSCC-based electrode.

When used in this application, the terms “pressure sensitive conductive composite” and “PSCC” mean a pressure sensitive conductive composite that has unique electrical properties as follows: the electrical resistance of the PSCC varies inversely in proportion to the pressure that is applied to the PSCC. The PSCC material that is most useful with the present invention has a high electrical resistance when not under stress (that is, in a quiescent state), and yet the same PSCC material starts to become conductive under pressure, and indeed, the electrical resistance may fall to less than one ohm (1Ω) when under sufficient pressure. When in a quiescent state, the PSCC material preferably has a resistance that is greater than 100,000 ohms, and more preferably, greater 1M ohms, and most preferably, the PSCC material is a non-conductor in its quiescent state (e.g., having a resistance greater than 10M ohms). Preferably, the PSCC material will also meet cytotoxity, hemolysis, systemic toxicity and intracutaneous injection standards.

The present invention will work with various pressure sensitive conductive composite materials. For example, U.S. Pat. No. 6,999,821 (which is incorporated by reference herein as if fully set forth below) discloses a conductor-filled polymer that may be useful in the present invention. As disclosed therein, conductor-filled polymers may include presently available materials approved for implantation in a human body such as silicone rubber with embedded metallic, carbon or graphite particles or powder. Silver filled silicone rubbers of the kind manufactured by NuSil or Specialty Silicone Products, modified so as to be approved for implantation, are of potential utility. An example is silver-coated, nickel-filled silicone rubber sold as NuSil R2637. The substrate need not be silicone; for example, it is contemplated that other insulating or weakly conductive materials (e.g., non-conductive elastomers) may be embedded with conductive materials, conductive alloys and/or reduced metal oxides (e.g., using one or more of gold, silver, platinum, iridium, titanium, tantalum, zirconium, vanadium, niobium, hafnium, aluminum, silicone, tin, chromium, molybdenum, tungsten, lead, manganese, beryllium, iron, cobalt, nickel, palladium, osmium, rhenium, technetium, rhodium, ruthenium, cadmium, copper, zinc, germanium, arsenic, antimony, bismuth, boron, scandium and metals of the lanthanide and actinide series and if appropriate, at least one electroconductive agent). The conductive material may be in the form of powder, grains, fibers or other shaped forms. The oxides can be mixtures comprising sintered powders of an oxycompound. The alloy may be conventional or for example titanium boride.

Other examples of an acceptable PSCCs for use in the present invention include quantum tunneling composites ("QTC"), such as those available through Peratech Ltd. (of Darlington, UK), including the QTC pill, the QTC substrate and the QTC cables. The QTC materials designed by Peratech Ltd. have variable resistance values that range from >10M ohms (in the absence of stress) to <1 ohm when under pressure. Ideally, the QTC would meet cytotoxity, hemolysis, systemic toxicity and intracutaneous injection standards.

Other examples of PSCC materials that may be used in the present invention include the conductive polymers described and disclosed in U.S. Pat. No. 6,646,540 ("Conductive Structures"); U.S. Pat. No. 6,495,069 ("Polymer Composition"); and U.S. Pat. No. 6,291,568 ("Polymer Composition"); all of the foregoing patents are incorporated by reference as if set forth below in their entireties. These materials as described has having a variable resistance of $>10^{12}$ Ohms before any stress is applied to less than 1 ohm when finger pressure is applied.

As a result of this unique property, PSCC materials may be described as having an ability to transform from an effective insulator to a metal-like conductor when deformed by compression, twisting, or stretching. The electrical response of a PSCC can be tuned appropriately to the spectrum of pressures being applied. Its resistance range often varies from greater than 10 MΩ to less than 1Ω. The transition from insulator to conductor often follows a smooth and repeatable curve, with the resistance dropping monotonically to the pressure applied. Moreover, the effect is reversible in the sense that once the pressure is removed, the electrical resistance is also restored. Thus, a PSCC may be transformed from an insulator to a conductor, and back to an insulator, simply by applying the appropriate pressure. PSCCs have been known to carry large currents (up to 10 Amps) and support large voltages (40 V and higher).

Preferably, the PSCC being used in connection with the present invention can transform from an insulator (that is, conducting little or no current) to an effective conductor simply by applying a small change in pressure to the PSCC. For example, by applying pressure with a hand, or more particularly, with a finger, a surgeon can transform the PSCC from an insulator to a conductor to permit contact sensing.

The PSCC used in the present invention may also be chosen or customized to be of a specific pressure sensitivity such that the transformation from an insulator to a conductor occurs over a wide or narrow range of pressure. For example, highly sensitive PSCCs, which register a sharp change in resistance with a finite amount of applied pressure, may be preferred for soft contact applications such as the atrial wall. Less sensitive PSCCs, which require more pressure to register the same amount of change in resistance, may be preferred for hard contact applications such as ablation in ventricular walls.

Because a PSCC's resistance drops monotonically as pressure increases, a PSCC electrode is able to deliver energy for ablation gradually, and then increasingly as pressure increases. Thus, the present invention permits ablation with a "soft start" and self-regulation of ablation current based on contact pressure.

The present invention permits the creation of an electrode fabricated of a PSCC that can differentiate between a soft and a hard push. Such a device can be used to switch, for example, an ablation electrode in response to a concentrated pressure while ignoring the general background pressure. Alternatively, such a device can "turn on" and deliver electrical energy that is already present within the device. Thus, by utilizing electrodes made with PSCCs, the present invention permits an electrode for delivering electrical energy for ablation, and indeed, may be designed for self actuation to deliver the electrical energy once the applied pressure exceeds a certain threshold.

Because a PSCC electrode may be used to deliver ablation with a "soft start," the PSCC electrode of the present invention may be used in direct contact with the target tissue, thereby eliminating the physical gap that sometimes exists with other ablation electrodes. Eliminating the gap reduces the possibility of arcing, and thereby improves the safety and efficacy of ablation.

The unique properties of a PSCC permit the creation of novel and pressure-sensitive current-control devices for the direct control of electrodes for various forms of electrical energy, including RF energy. The unique properties permit the creation of novel and pressure-sensitive sensors to assess contact between the sensors and tissue that may be the subject of ablation.

Figure 1B:
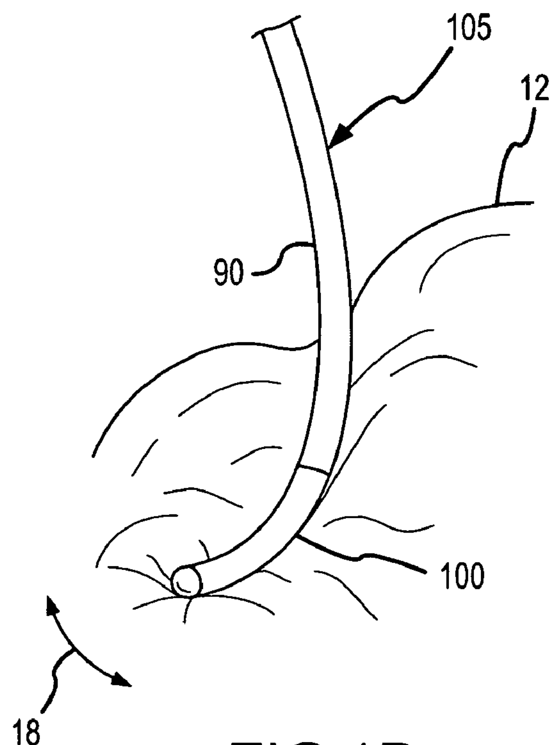

FIGS. 1A and 1B illustrate a sample embodiment of the present invention. As illustrated in FIGS. 1A and 1B, PSCC electrode 105 includes a catheter shaft 90 and a contact surface 100 that extends from catheter shaft 90. In this embodiment, PSCC electrode 105 is flexible such that when it comes into contact with tissue 12, PSCC electrode 105 is deflected in direction 18 as illustrated in FIG. 1*b*, and the deflection permits the activation of PSCC electrode 105 based on a degree of contact between PSCC electrode 105 and tissue 12.

Figure 2:
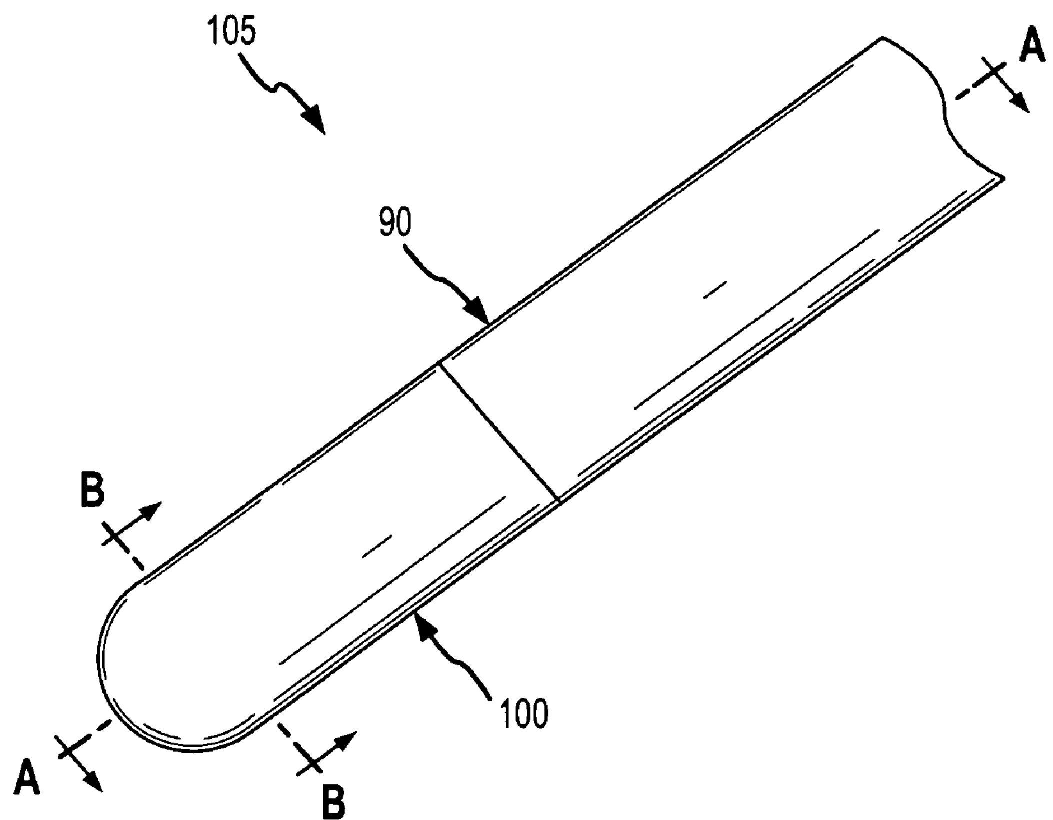
FIG. 2 is a side view drawing of an exemplary catheter having a PSCC electrode.

FIG. 2 is a close-up of the sample embodiment depicted in FIGS. 1A and 1B. FIG. 2 illustrates cross-sectional reference lines A-A and B-B, which will be used to illustrate preferred embodiment of the present invention.

Figure 3A:
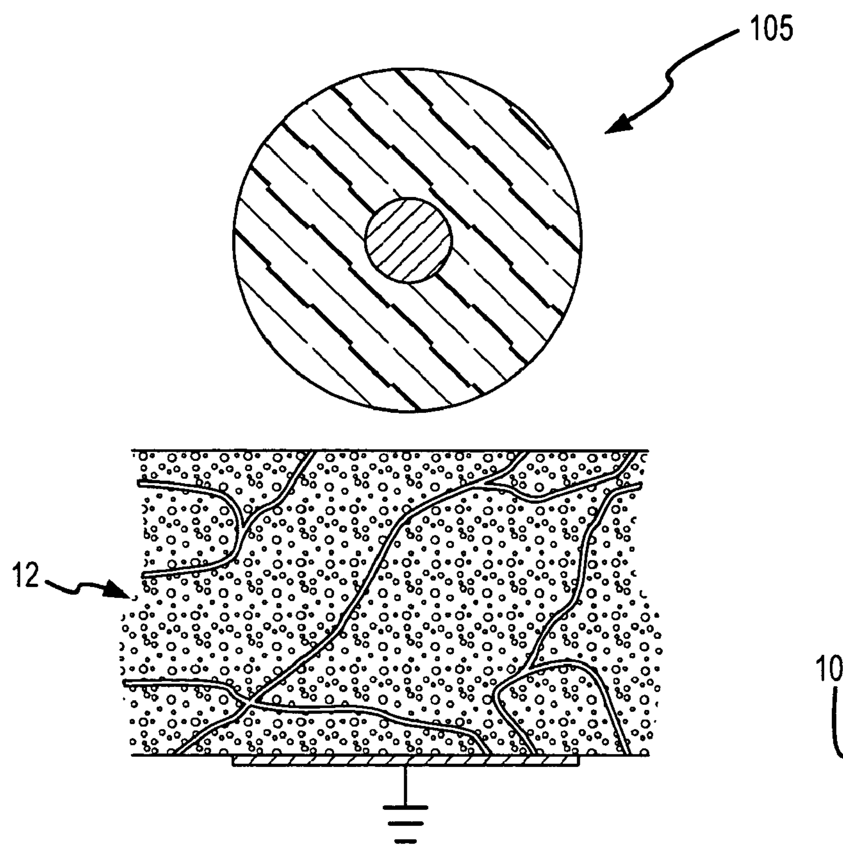
FIGS. 3A and 3B are cross sectional views that demonstrate the contact pressure at the electrode-tissue interface.
Figure 3B:
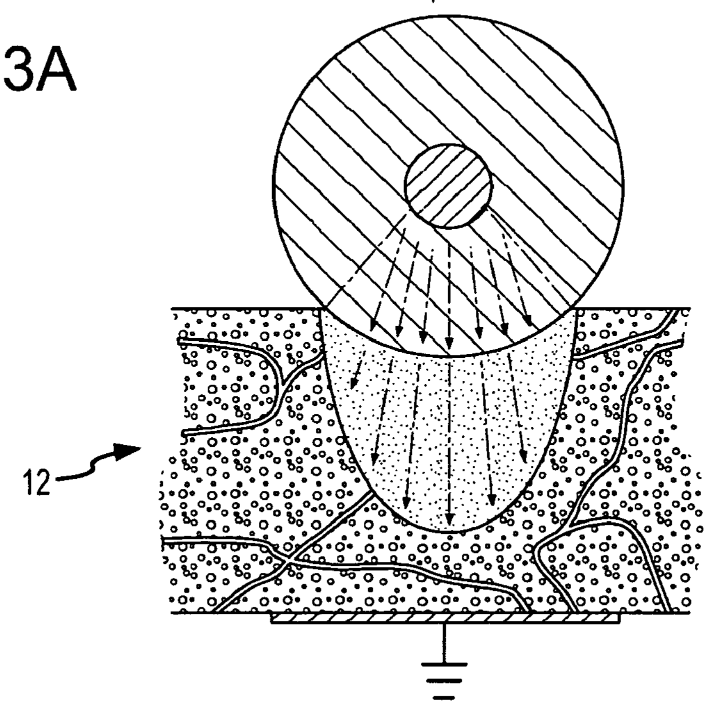

As illustrated in FIG. 3A, when the PSCC electrode is in a relatively contact free environment (such as air, or in the flowing blood stream while inside a blood vessel or heart chamber), the PSCC is an insulator. When used for an ablation application, however, the PSCC electrode is placed against tissue as illustrated in FIG. 3B. As the contact pressure increases, the PSCC becomes conductive and permits the degree of contact to activate and/or control operation of PSCC electrode. Because of the unique properties of a PSCC, only that portion of the PSCC electrode that is in contact with the tissue becomes conductive. Those portions which are not in direct contact with the tissue, such as the region facing the blood, remain non-conductive, thereby mitigating any current leakage that may cause coagulum and thrombus formation.

The resistance of a PSCC electrode changes anisotropically, based on the variation of the contact pressure on the PSCC electrode. Thus, as illustrated in FIG. 3B, the contact pressure at the electrode-tissue interface is maximum at the point (or line) of normal incidence and gradually decreases along the arc of contact to zero at the edge of the contact. Because of its ability to direct RF energy to the point of contact, the electrode is omni-directional in use, but tissue-directional in application. The RF energy passes mostly into the tissue and minimally into the blood. This offers significant advantages, including increased efficiency, over other ablation electrodes.

Figure 4A:
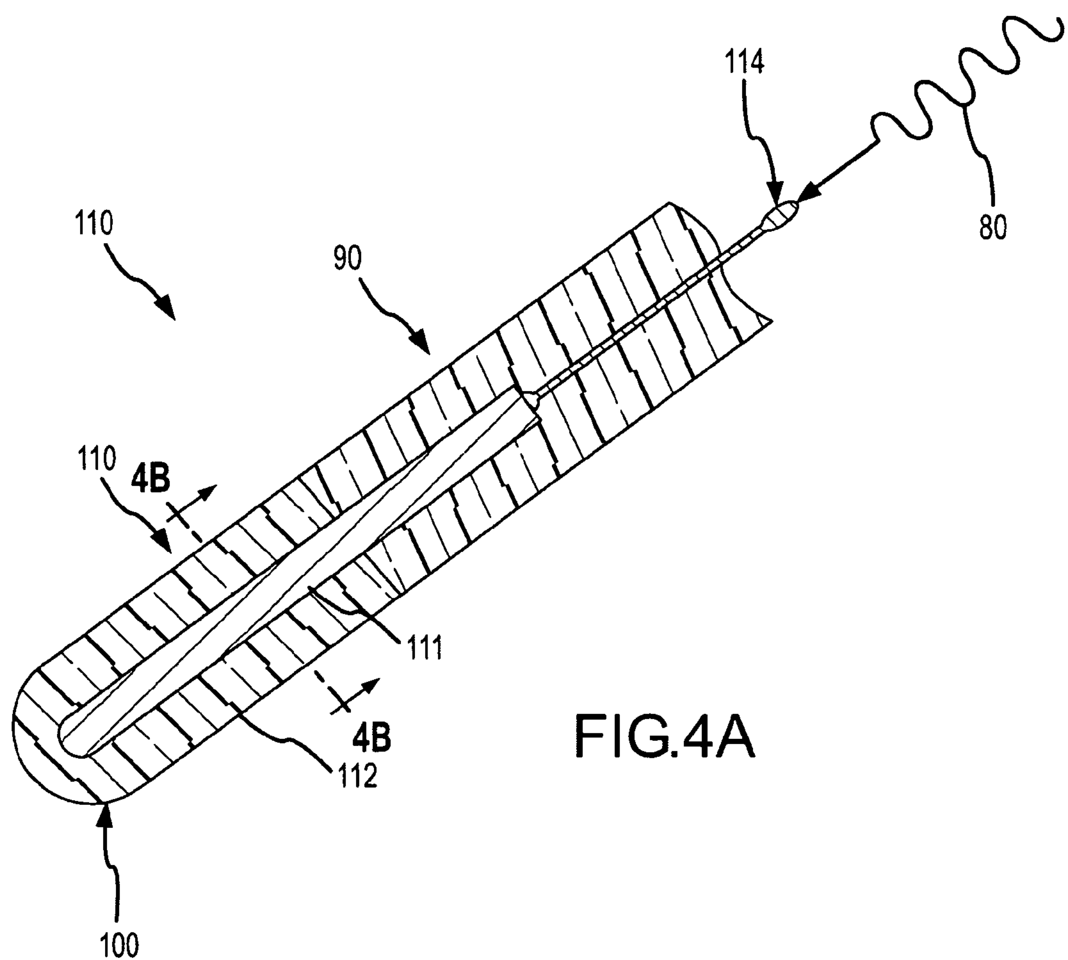
FIGS. 4A and 4B are cross-sectional views of a preferred embodiment of a catheter having a PSCC electrode.
Figure 4B:
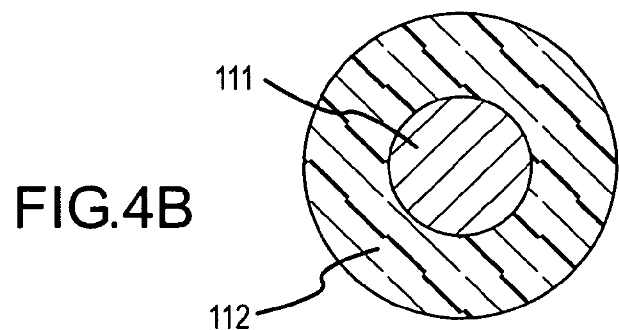

FIGS. 4A and 4B illustrate a preferred embodiment of the present invention, revealing two cross sectional drawings taken along the reference lines of A-A and B-B as labeled in FIG. 2. In this preferred embodiment, the PSCC electrode 110 comprises: catheter shaft 90 and a contact surface 100 that extends from catheter shaft 90. Catheter shaft 90 may be either conductive or non-conductive, and preferably, catheter shaft 90 is non-conductive. In this embodiment, the PSCC forms the working surface of the electrode that is used for ablation therapy. As depicted in FIGS. 4A and 4B, PSCC electrode 110 comprises: flexible inner conductive core 111; and an outer PSCC substrate layer 112, which is mechanically and electrically coupled to the flexible inner conductive core 111. Flexible inner conductive core 111 may include a flat top (like the top of a right cylinder), or optionally it may include a portion of a sphere on its distal end as illustrated in FIG. 4A. Flexible inner conductive core 111 may be connected to an electrical conductor 114, which may be connected to an RF generator (e.g., RF current source 80). In use, this preferred embodiment is used to ablate tissue (not shown) to which a reference electrode (not shown) has been attached. PSCC electrode 110 ablates tissue by delivering ablation energy through inner conductive core 111. Preferably, the reference electrode is grounded to an electrical ground.

As an alternative to the flexible embodiment discussed in the preceding paragraph, it is contemplated that the same structural design may be used to produce a less flexible (or even rigid) ablation device. For example, PSCC electrode 110 may comprise: a rigid inner conductive core 111; and an outer PSCC substrate layer 112, which is electrically coupled to the inner conductive core 111. Inner conductive core 111 may be connected to an electrical conductor 114, which may be connected to an RF generator (e.g., RF current source 80). In use, this preferred embodiment is used to ablate tissue (not shown) to which a reference electrode (not shown) has been attached. PSCC electrode 110 ablates tissue by delivering ablation energy through inner conductive core 111. While the inner conductive core is rigid, the PSCC layer is deformable such that when the ablation electrode is pressed into the tissue, the PSCC becomes conductive and delivers RF energy to the tissue for ablation purposes. In this embodiment, the PSCC may be coated with one or more outer electrically-conductive layers (which may be rigid or flexible). In this further modification, the PSCC layer is sandwiched between at least two conductive coatings, and thus under pressure, the RF energy is delivered to the tissue via the rigid inner conductive core, the compressible PSCC layer, and the one or more outer electrically-conductive layers.

Figure 5A:
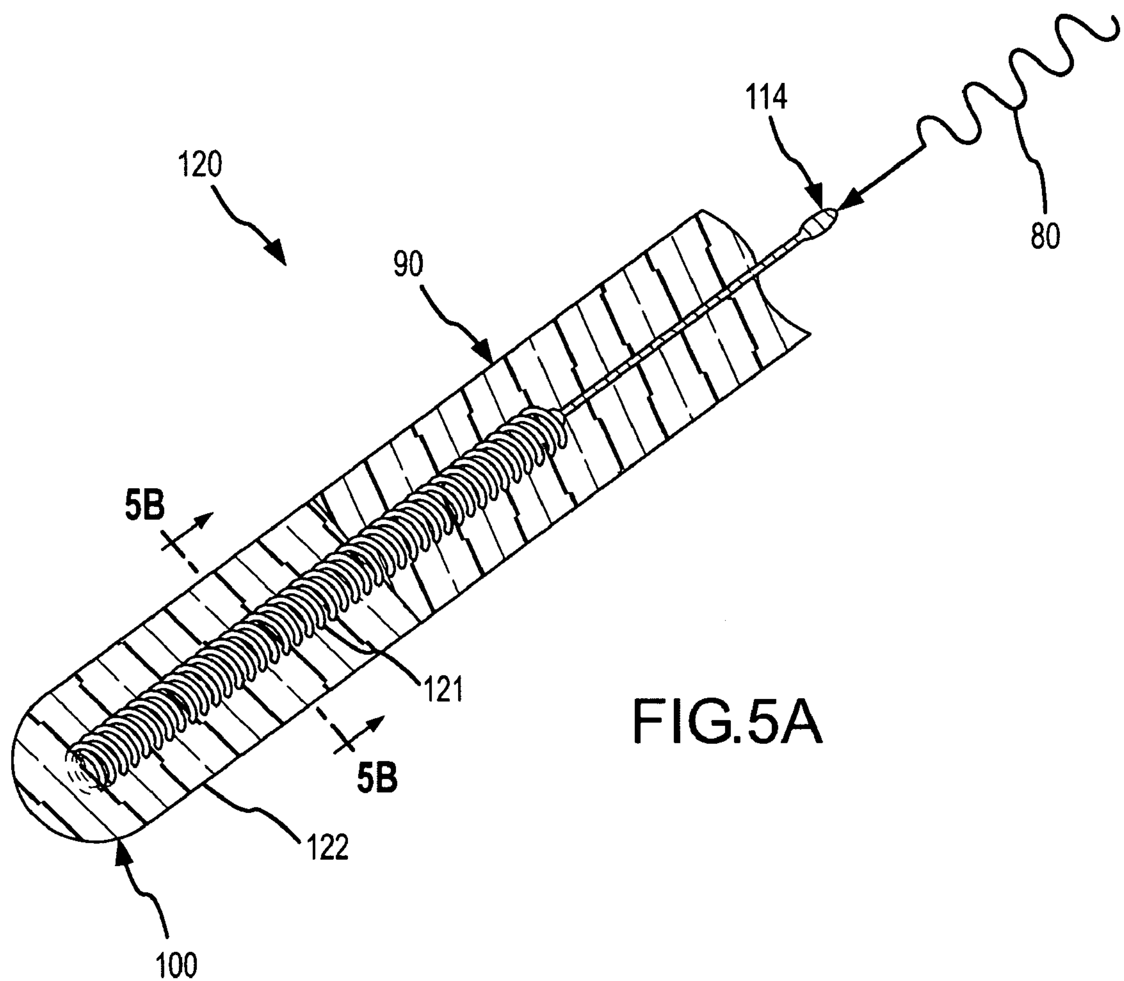
FIGS. 5A and 5B are cross-sectional views of another preferred embodiment in which the PSCC electrode is in the shape of a helix.
Figure 5B:
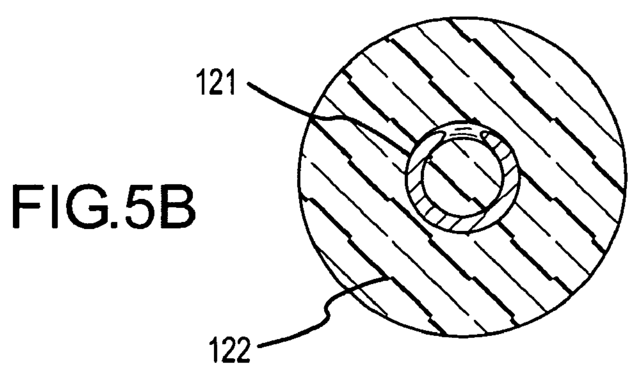

FIGS. 5A and 5B illustrate another preferred embodiment of the present invention, revealing two cross sectional drawings taken along the reference lines of A-A and B-B as labeled in FIG. 2. PSCC electrode 120 extends from a catheter shaft 90, and PSCC electrode 120 comprises: flexible inner conductive coil 121 in the shape of a helix; and a PSCC substrate layer 122 within which the inner conductive coil 121 is located. Flexible inner conductive coil 121 is connected to an electrical conductor 114, which may be connected to an RF generator (e.g., RF current source 80). In use, this preferred embodiment is used to ablate tissue (not shown) to which a reference electrode (not shown) has been attached. PSCC electrode 120 ablates tissue by delivering ablation energy through inner conductive coil 121. Preferably, the reference electrode is grounded to an electrical ground. PSCC electrode 120, when pressure is asserted by tissue against contact surface 100, which reduces the internal impedance of the PSCC substrate.

Figure 6A:
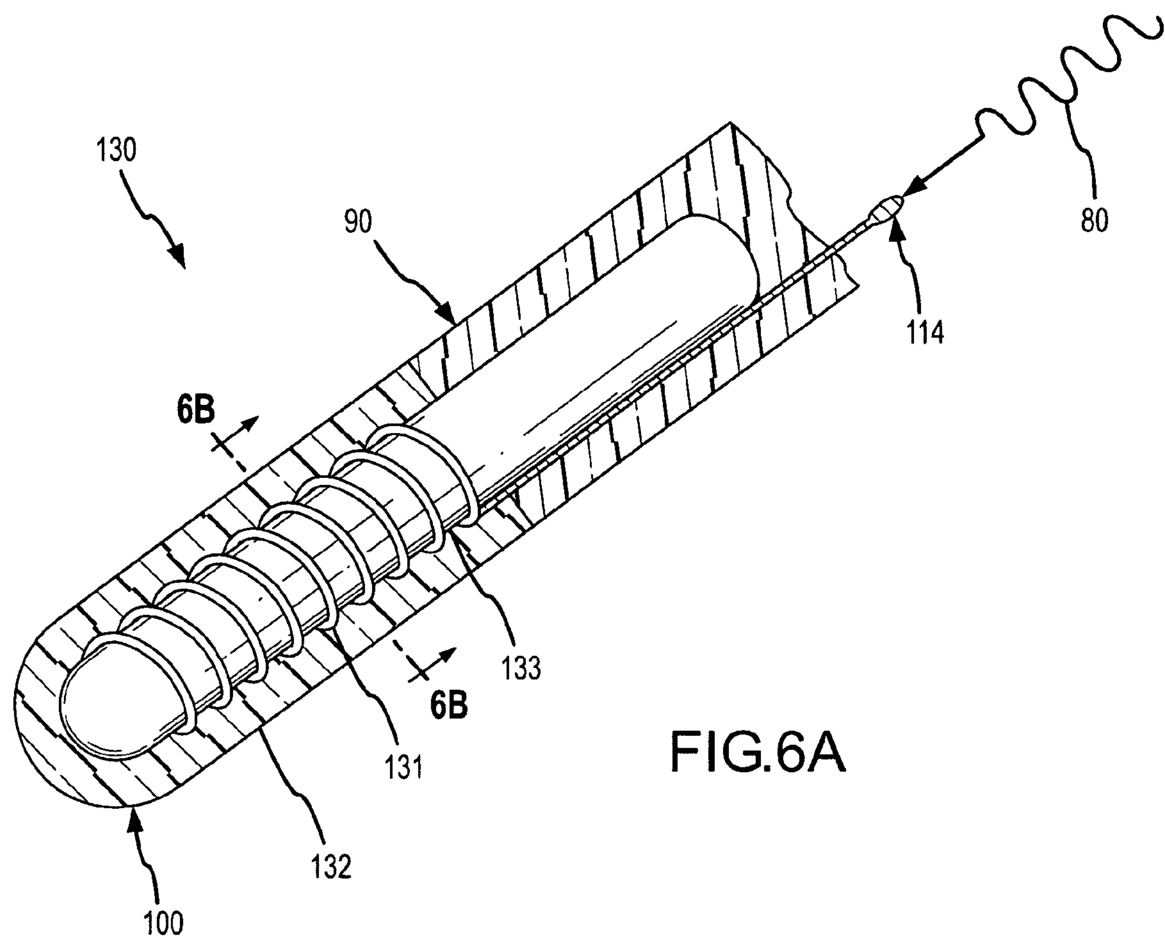
FIGS. 6A and 6B are cross-sectional views of another preferred embodiment in which the PSCC electrode is located about an inner conductive core.
Figure 6B:
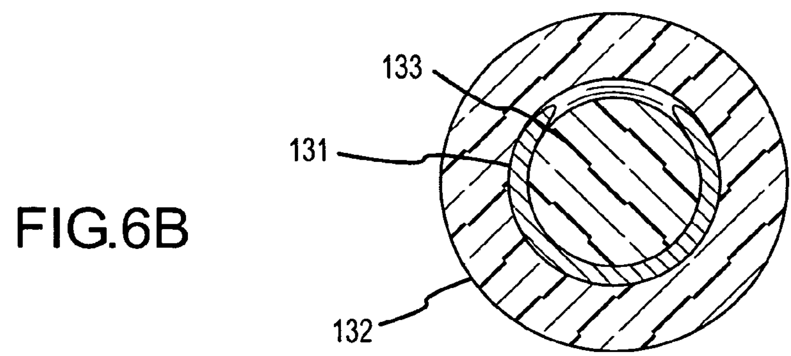

FIGS. 6A and 6B illustrate yet another preferred embodiment of the present invention, revealing two cross sectional drawings taken along the reference lines of A-A and B-B as labeled in FIG. 2. PSCC electrode 130 extends from a catheter shaft 90, and PSCC electrode 130 comprises: flexible inner conductive coil 131 in the shape of a helix; an outer PSCC substrate layer 132; and an electrically insulative flexible shaft 133 located within the helix of the flexible inner conductive coil 131. Flexible shaft 133 may optionally include a portion of a sphere on its distal end as shown in FIG. 6A. Flexible inner conductive coil 131 is connected to an electrical conductor 114, which may be connected to an RF generator (e.g., RF current source 80). In use, this preferred embodiment is used to ablate tissue (not shown) to which a reference electrode (not shown) has been attached. PSCC electrode 130 ablates tissue by delivering energy through inner conductive coil 131. Preferably, the reference electrode is grounded to an electrical ground reference signal. PSCC electrode 130, when pressure is asserted by tissue against contact surface 100, which reduces the internal impedance of the PSCC substrate.

Figure 7A:
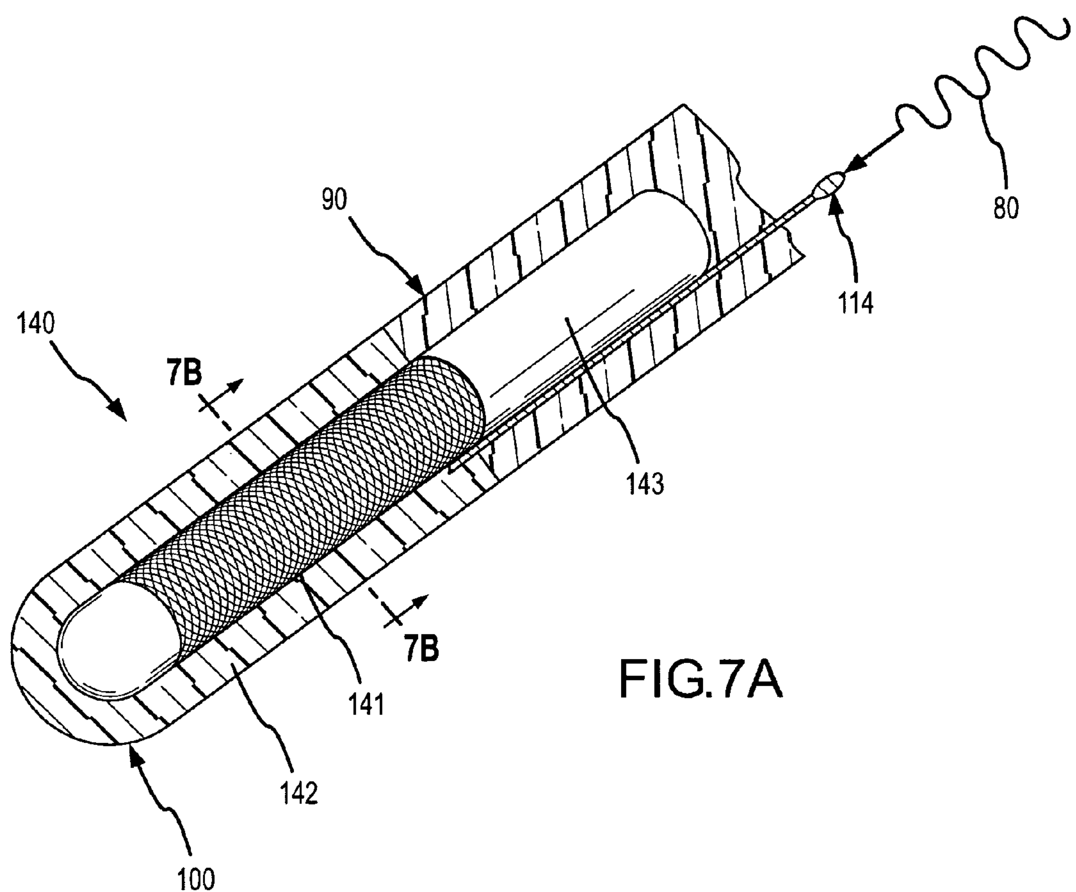
FIGS. 7A and 7B are cross-sectional views of another preferred embodiment in which the PSCC electrode is in the shape of a mesh.
Figure 7B:
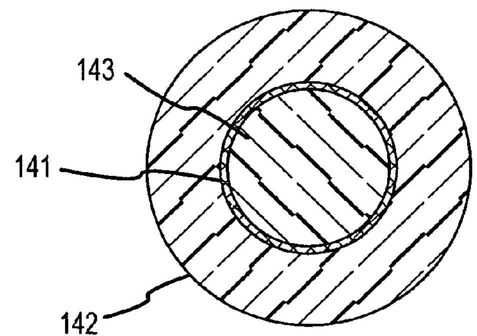

FIGS. 7A and 7B illustrate yet another preferred embodiment of the present invention, revealing two cross sectional drawings taken along the reference lines of A-A and B-B as labeled in FIG. 2. PSCC electrode 140 extends from a catheter shaft 90, and PSCC electrode 140 comprises: flexible inner conductive sheath 141 formed of a mesh; an outer PSCC substrate layer 142; and an electrically insulative flexible shaft 143 located interiorly of the flexible inner conductive sheath 141. Flexible shaft 143 may optionally include a portion of a sphere at its distal end as shown in FIG. 7A. Flexible sheath 141 is connected to an electrical conductor 114, which may be connected to an RF generator (e.g., RF current source 80). In use, this preferred embodiment is used to ablate tissue to which a reference electrode (not shown) has been attached. PSCC electrode 140 ablates tissue by delivering energy through the flexible sheath 141. Preferably, the reference electrode is grounded to an electrical ground reference signal.

Figure 8A:
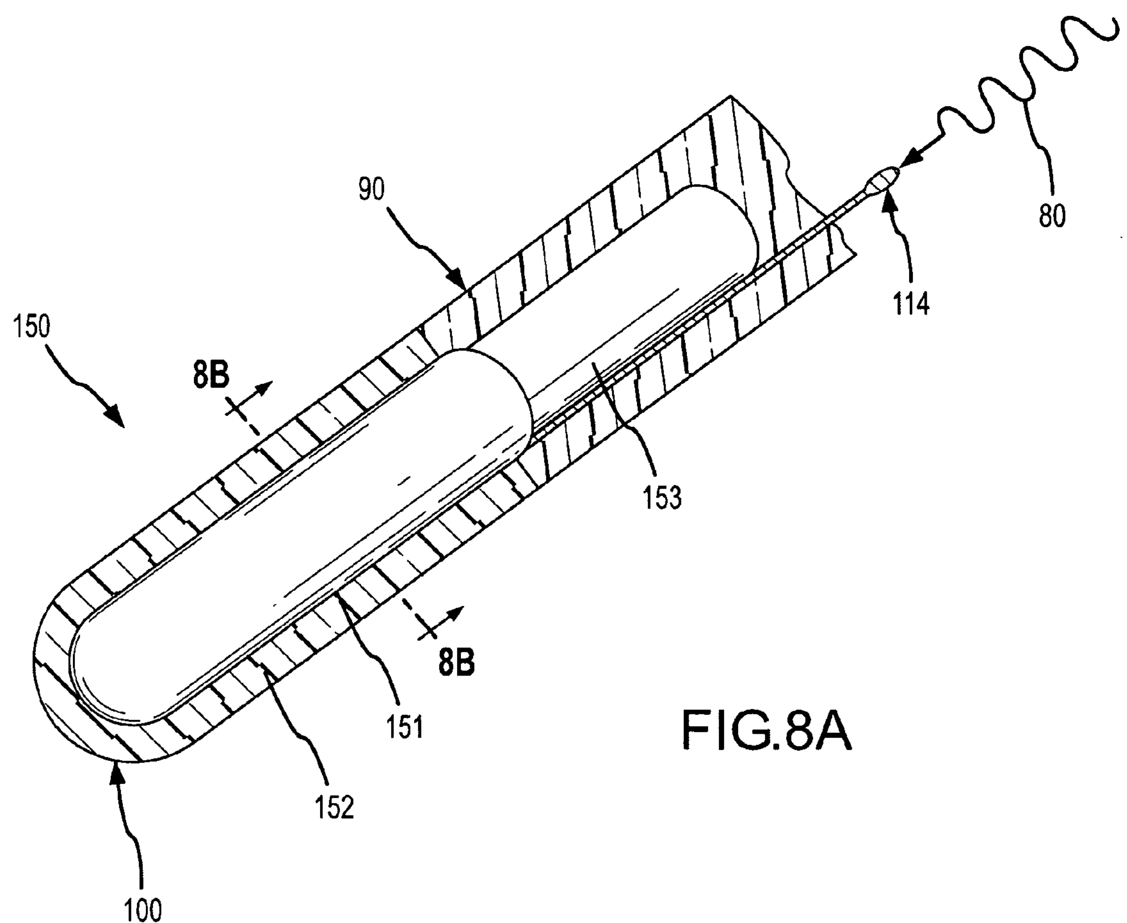
FIGS. 8A and 8B are cross-sectional views of another preferred embodiment in which the PSCC electrode is formed as an outer substrate layer.
Figure 8B:
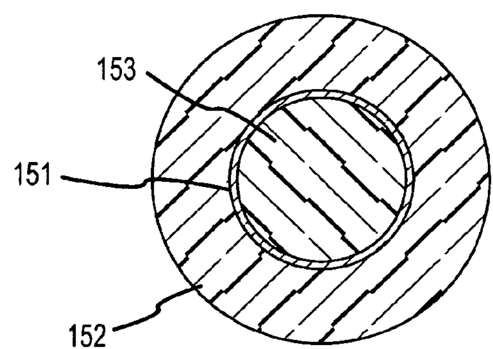

FIGS. 8A and 8B illustrates yet another preferred embodiment of the present invention, revealing two cross sectional drawings taken along the reference lines of A-A and B-B as labeled in FIG. 2. PSCC electrode 150 extends from a catheter shaft 90, and PSCC electrode 150 comprises: an electrically insulative flexible shaft 153; a flexible inner conductive layer 151 (formed, for example, as a coating and/or wrap around flexible shaft 153); and an outer PSCC substrate layer 152. Electrically insulative flexible shaft 153 and flexible inner conductive layer 151 may optionally include a portion of a sphere at their respective distal ends (as illustrated in FIG. 8A). Flexible inner conductive core 151 is connected to an electrical conductor 114, which may be connected to an RF generator (e.g., RF current source 80). In use, this preferred embodiment is used to ablate tissue (not shown) to which a reference electrode (not shown) has been attached. PSCC electrode 150 ablates tissue by delivering ablation energy through the flexible inner conductive core 151. Preferably, the reference electrode is grounded to an electrical ground reference signal.

Figure 9A:
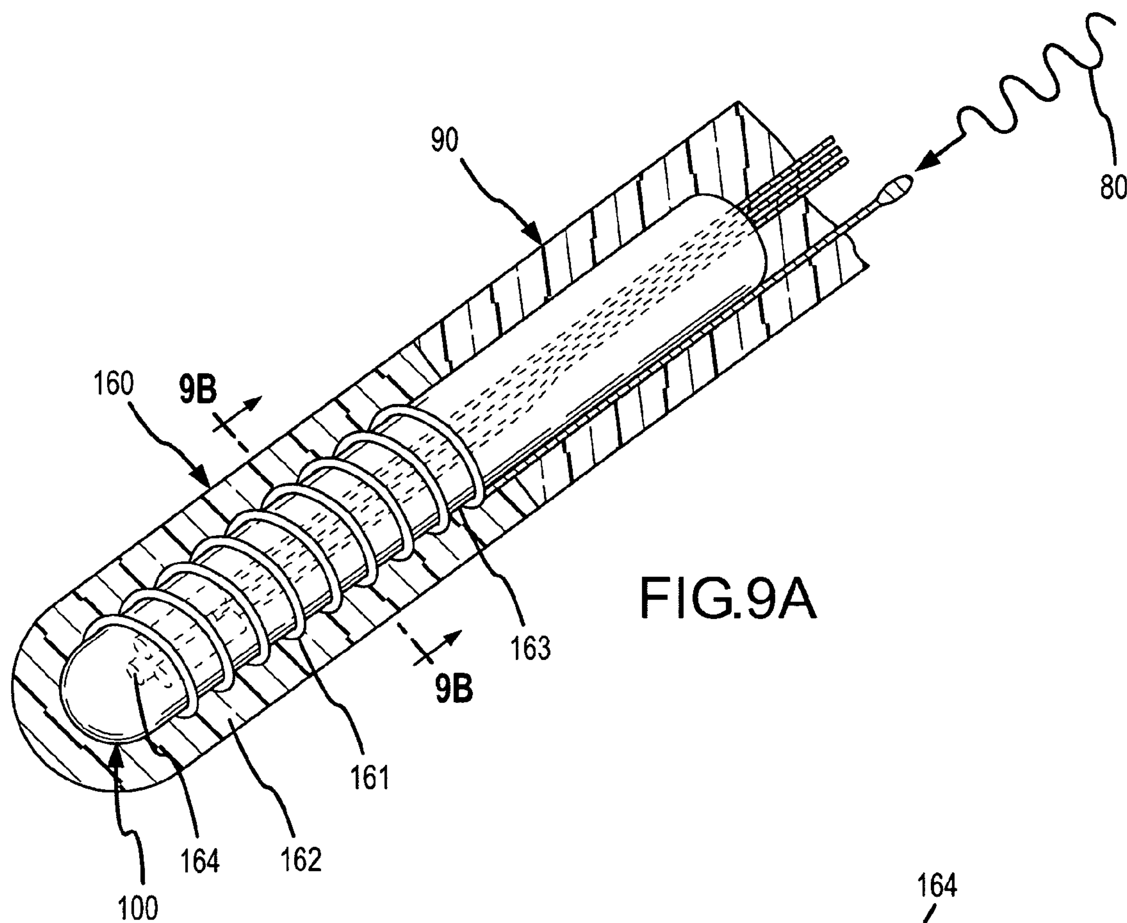
FIGS. 9A and 9B are cross-sectional views of yet another preferred embodiment of the invention with thermal sensing.
Figure 9B:
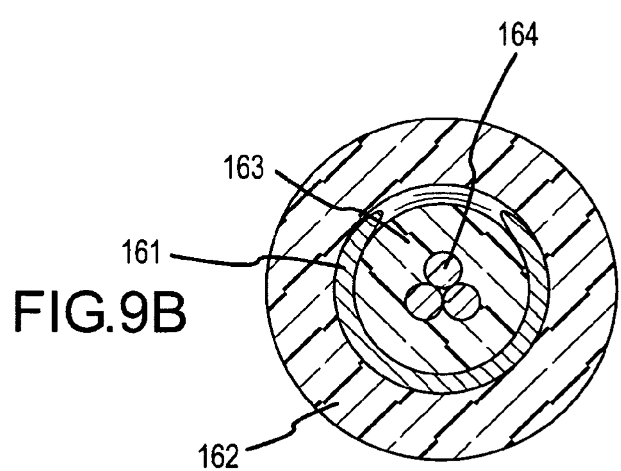

FIGS. 9A and 9B illustrates yet another preferred embodiment of the present invention, revealing two cross sectional drawings taken along the reference lines of A-A and B-B as labeled in FIG. 2. PSCC electrode 160 extends from a catheter shaft 90, and PSCC electrode 160 comprises: a thermally conductive, electrically insulative, flexible shaft 163; a flexible inner conductive layer 161 (formed, for example, as a coating and/or wrap around flexible shaft 163, or as illustrated in FIG. 9, a helix); an outer PSCC substrate layer 162; and a plurality of thermal sensors 164 located within the thermally conductive, electrically insulative, flexible shaft 163 to measure temperatures at various locations therein. Electrically insulative flexible shaft 163 and flexible inner conductive layer 161 may optionally include a portion of a sphere at their respective distal ends (as illustrated in FIG. 9A). Flexible inner conductive coil 161 is connected to an electrical conductor 114, which may be connected to an RF generator (e.g., RF current source 80). In use, this preferred embodiment is used to ablate tissue (not shown) to which a reference electrode (not shown) has been attached. PSCC electrode 160 ablates tissue by delivering ablation energy through the flexible inner conductive coil 161. Preferably, the reference electrode is grounded to an electrical ground reference signal. As one of ordinary skill can appreciate, temperature sensors 164 (such as thermistors, thermocouplers or other temperature sensors) can be used to monitor operation temperature to help ensure effective and safe ablation treatment. For example, one or more temperatures may be used at a variety of locations, include e.g., at a distal end at the device to monitor a temperature that is at least in part reflective of the tissue temperature, or even within the electrically insulative shaft. Other potential locations include the use of a temperature sensor located at a location where the cooling fluid enters the device. Of course, temperature sensors may be located at additional locations.

Figure 10A:
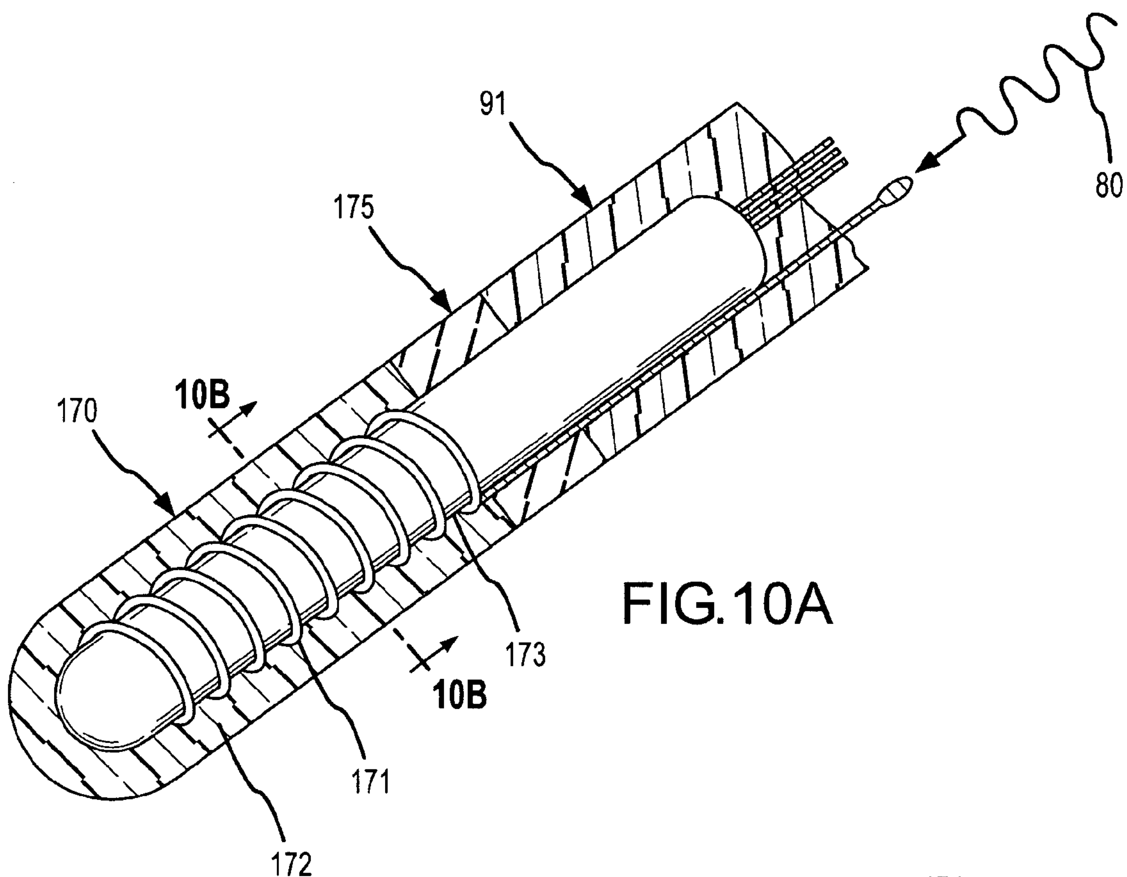
FIGS. 10A and 10B are cross-sectional views of another preferred embodiment in which the PSCC electrode is adjacent a heat sink.
Figure 10B:
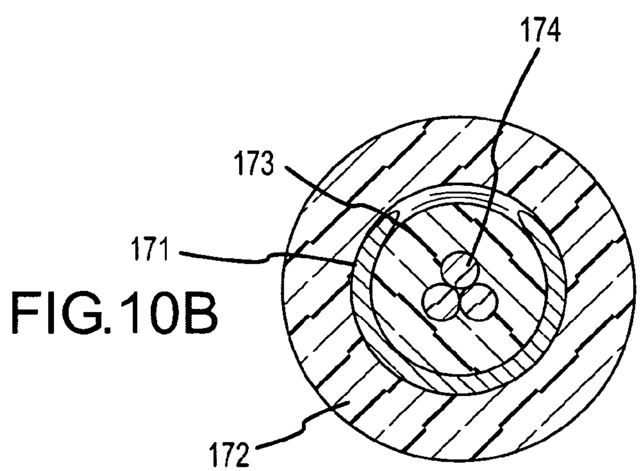

FIGS. 10A and 10B illustrates yet another preferred embodiment of the present invention, revealing two cross sectional drawings taken along the reference lines of A-A and B-B as labeled in FIG. 2. PSCC electrode 170 extends from a catheter shaft 90, and PSCC electrode 170 comprises: a thermally conductive, electrically insulative, flexible shaft 173; a flexible inner conductive layer 171 (formed, for example, as a coating and/or wrap around flexible shaft 173, or as illustrated in FIG. 10, a helix); an outer PSCC substrate layer 172; a heat sink 175 thermally coupled to flexible shaft 173; and a plurality of thermal sensors 174 located within the thermally conductive, electrically insulative, flexible shaft 173 to measure temperatures at various locations therein. Electrically insulative flexible shaft 173 and flexible inner conductive layer 171 may optionally include a portion of a sphere at their respective distal ends (as illustrated in FIG. 10A). Flexible inner conductive coil 171 is connected to an electrical conductor 114, which may be connected to an RF generator (e.g., RF current source 80). In use, this preferred embodiment is used to ablate tissue (not shown) to which a reference electrode (not shown) has been attached. PSCC electrode 170 ablates tissue by delivering ablation energy through the flexible inner conductive coil 171. Preferably, the reference electrode is grounded to an electrical ground reference signal. As one of ordinary skill can appreciate, temperature sensors 174 (such as thermistors, thermocouplers or other temperature sensors) can be used to monitor operation temperature to help ensure effective and safe ablation treatment. Heat sink 175 helps to prevent the electrode from overheating the electrode and the tissue.

Electrical conductor 114 may be implemented using a single conductive wire or multiple strands of wire. Preferably, the wires may be made of flexible conductive materials which allow the surface contacting area to be bent and formed into various shapes to provide better contact to the tissue. Acceptable materials include, but are not limited to, stainless steel, nickel titanium (nitinol), tantalum, copper, platinum, iridium, gold, or silver, and combinations thereof. Preferably, the material used to manufacture the conductive element is a bio-compatible electrically conductive material, such as platinum, gold, silver, nickel titanium, and combinations thereof. Other electrically conductive materials coated with bio-compatible materials may also be employed, including for example, gold-plated copper. Finally, it is also contemplated that electrically conductive polymers may also be used provided they are bio-compatible or coated with a bio-compatible material.

The present invention permits the construction of a flexible, pressure sensitive RF ablation electrode that can be used in a wide variety of different tissue environments, including for example, tissues having varying degrees of elasticity and contour.

The present invention permits the construction of a flexible electrode that responds to pressure that is applied to the electrode, for example, pressure that may be applied to the electrode by the myocardium. Such electrodes may be used to respond to pressure that is applied directly to the PSCC component (for example, when the PSCC component is located at the most distal portion of a catheter), or to pressure that is applied indirectly to the PSCC (for example, when an electrode tip id disposed between the PSCC component and the tissue). When used in conjunction with an electrode tip, it is desired that the electrode tip be formed of a rigid, electrically conductive material. This will permit the electrode tip to transfer pressure from the electrode tip to the PSCC component. Optionally, one or more additional pressure transfer elements may be used, for example, between the electrode tip at a distal end and the PSCC component located at a more proximal end. In the case where a PSCC component is positioned within a catheter, the PSCC component is preferably used to respond to pressure that is applied axially to catheter. Of course, the PSCC component could be oriented in order to respond to pressure that is applied transversely to the catheter.

While the preferred embodiments disclosed in the attached figures disclose an electrode that is generally cylindrical in shape, the present invention also contemplates that the electrode may be formed into various shapes to better fit the contour of the target tissue. In one embodiment, for example, the electrode can be made long enough to strap around and form a noose around the pulmonary veins in epicardial applications. Particularly, electrical conductor 114 that is coupled to the RF energy source may be formed into a desired shape and then the PSCC layer will be formed over the conductive element in the preferred shape. For example, the electrode may be shaped like a spatula for certain applications, including for example, minimally invasive sub-xyphoid epicardial applications, where the spatula shape will permit easy placement and navigation in the pericardial sac. Because PSCC can be made as a flexible material, it can be used for form electrodes having a great variety of shapes, including a spatula.

Alternatively, the electrically conductive element that is coupled to the RF energy source (for example, 111, 121, 131, 141, 151, 161 and 171) may be formed using shape-memory retaining material, such as nitinol, which would permit the electrode to be fitted to specific preset geometries, such as the ostium of a pulmonary vein, such that the electrode is shaped to provide a desired contact pressure pattern on the tissue due to the deformation of the wire when pressed against the tissue.

Similarly, while the reference to insulative shaft (for example, 133, 143, and 153) is generally used in connection with a generally cylindrical member, it is contemplated by the present invention that the insulative shaft could be in a geometric shape other than a cylinder, including, for example, a noose, a spatula, or the shape of the ostium of a pulmonary vein. For purposes of this application, the term "insulative shaft" is intended to encompass shapes in addition to a cylindrical shaft.

Whenever it is desired that the conductive element that is coupled to the RF energy source be formed in the shape of a helix, such as is the case with elements 121, 131, 161 and 171, the coil may be chosen to be of a specific stiffness (i.e., having a characteristic spring constant) that would allow the coil to exert a desired amount of pressure on the PSCC when the electrode bends or deflects upon contact with the tissue. One of skill in the art would understand that the degree of desired contact pressure would depend in part upon the elastic property of the tissue being contacted with the electrode. For example, the atrial wall may require less contact pressure than the ventricular wall. Thus, electrodes of varying stiffness can be designed for application in different tissues and different regions of the heart.

In some embodiments, for example, as depicted in FIGS. 5, 6 and 7, the conductive element may be mounted on an insulative shaft. The conductive element can be shaped in any number of ways, including for example, a coil, mesh, coating or wrap. The insulative shaft provides additional mechanical support in applications that require greater amounts of axial force and torque. The insulative shaft may be made of any electrically insulative material, including, for example, polyurethane. Preferably, the insulative shaft is made of a biocompatible, electrically insulative material.

Generally, flexibility is a very desirable characteristic in a catheter. Some applications, however, may require a less flexible and/or rigid catheters. Thus, as an alternative to the flexible embodiments discussed above, it is contemplated that the same structural design may be used to produce a less flexible (or even rigid) ablation device. For example, the PSCC electrode may utilize a rigid core—instead of a flexible core. It may be solid conductive core of varying degrees of rigidity, or a non-conductive core coated with a conductive layer such that the combination achieves a desired degree of rigidity. A PSCC substrate layer may then be applied to the core such that when the electrode is pressed against tissue, the PSCC becomes a conductor and electrically couples the conductive core (or layer, as the case may be) to the tissue via the PSCC. In this alternative embodiment, the PSCC may be coated with one or more outer electrically-conductive layers (which may be rigid or flexible). In this further modification, the PSCC layer is sandwiched between at least two conductive coatings, and thus under pressure, RF energy may be delivered to the tissue via the compressible PSCC layer.

In other embodiments, for example, as depicted in FIGS. 8A and 9A, the conductive element is mounted on an electrically insulative but thermally conductive shaft. The thermally conductive shaft would improve the cooling of the electrode and the electrode-tissue interface temperature during ablation by thermally conducting the heat from the interface to the ambient flowing blood in endocardial applications. In addition, the thermally conductive shaft can be instrumented with thermal sensors (for example, as depicted in Exhibits 8 and 9) that can be used for temperature controlled RF ablation. The thermally conductive shaft may be made of any electrically insulative, thermally conductive material, including, for example, CoolPoly® thermally conductive, electrically insulative plastic. Preferably, the thermally conductive shaft is made of a biocompatible, thermally conductive, electrically insulative material.

In yet another embodiment, for example, as depicted in FIG. 9, the cooling efficiency of the ablation electrode can be enhanced by mounting a heat sink 175 at the proximal end of the active electrode 170. The heat sink comprises a material with high thermal conductivity. The use of a heat sink may be particularly useful for small electrodes typically around 10 mm or less, or for sectioned electrodes that may give rise to hot spots. The heat sink may be made of any electrically insulative, thermally conductive material, including, for example, thermally conductive polyurethane (e.g., polyurethane with thermally conductive ceramic powder embedded therein), diamond, aluminum nitride, boron nitride, silicone, thermal epoxy and thermally conductive, electrically insulative plastics. Preferably, the thermally conductive shaft is made of a biocompatible, thermally conductive, electrically insulative material.

In yet another embodiment, the electrically insulative member may contain one or more passageways for carrying cooling fluids (e.g., saline solution) to the distal end of the electrode. Alternatively, one or more of the passageways may be further defined by a cooling tube made of the same material as, or a material different from, the insulative member. If a cooling tube is used in addition to the passageway, the portion of the cooling tube that is located within the catheter shaft is preferably thermally and electrically insulative, while the portion of the cooling tube that is located within the electrode is preferably thermally conductive. The thermally insulative tube inside the catheter shaft is to minimize the degree to which the cooling fluid is heated to body temperature as the result of thermal conduction through the catheter shaft wall as the fluid travels from the outside fluid source through the catheter shaft and to the electrode. The thermally conductive tube inside the electrode, on the other hand, is intended to cool the electrode and the electrode-tissue interface during ablation by thermally conducting the heat from the interface to the flowing fluid inside the tube.

In yet another embodiment, the electrically insulative member may contain one or more passageways for carrying cooling fluids to the actual electrode-tissue interface. The passageways include an inlet to the electrode, and an outlet at the distal end of the electrode. Moreover, one or more thermal sensors may be placed in the passageway, for example, to measure the temperature of the coolant at the inlet and at the outlet. The temperature difference between the inlet and outlet during ablation could be used to monitor the efficacy of the electrode-tissue interface cooling and also to perform temperature-controlled ablation. One or more of the passageways may alternatively be further defined by a cooling tube, which is made be made of the same material as, or a material different from, the insulative member. If a cooling tube is used in addition to the passageway, the portion of the cooling tube that is located within the catheter shaft is preferably thermally insulative, while the portion of the cooling tube that is located within the electrode is preferably thermally and electrically conductive. The thermally insulative tube inside the catheter shaft is to minimize the degree to which the cooling fluid is heated to body temperature as the result of thermal conduction through the catheter shaft wall as the fluid travels from the outside fluid source through the catheter shaft and to the electrode. The thermally conductive tube inside the electrode, on the other hand, is intended to cool the electrode and the electrode-tissue interface during ablation by thermally conducting the heat from the interface to the flowing fluid inside the tube.

Figure 11:
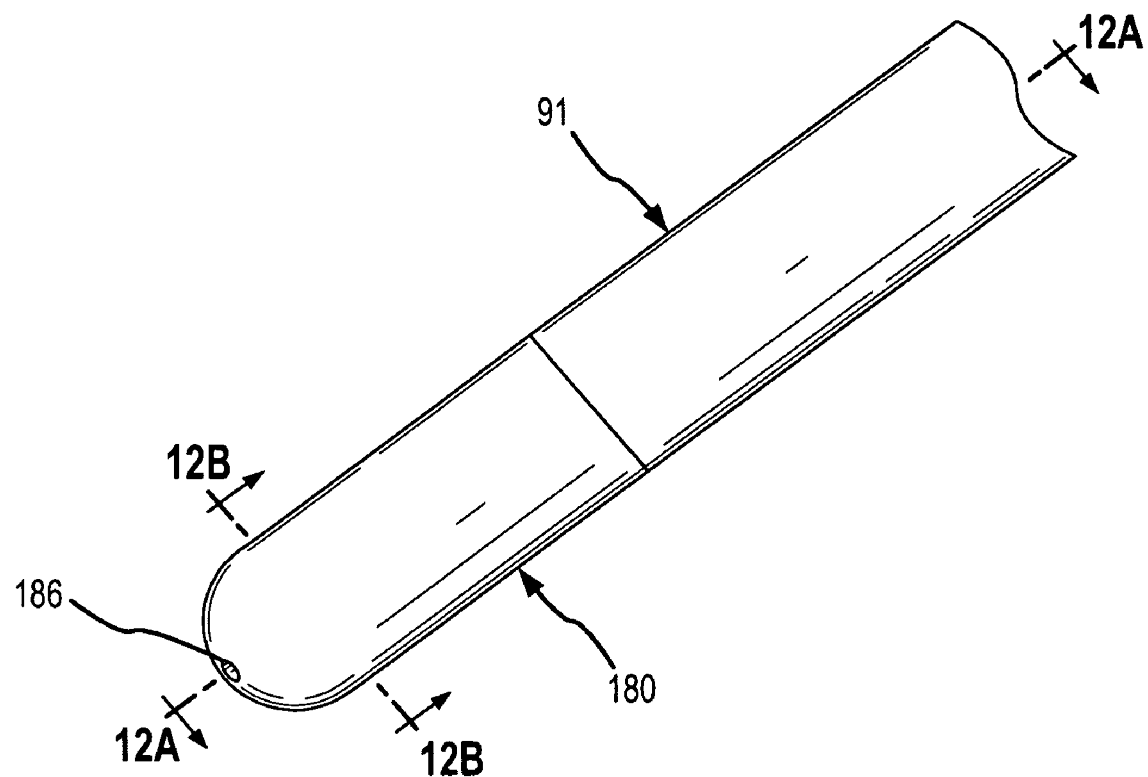
FIG. 11 is a side view of another preferred embodiment of the invention in which the catheter includes a coolant efflux hole.

FIG. 11 illustrates a specific preferred embodiment for the invention of the present application. PSCC electrode 180 extends from a catheter shaft 91 and is connected to an RF energy source (not shown). PSCC electrode 210 further comprises coolant efflux hole 186 that permits the coolant flowing through the core of the catheter from stagnating (and thus heating) inside the catheter. The efflux hole helps to ensure that a fresh supply of coolant is available to keep the working portion of the catheter cool. The use of efflux hole 186 could be utilized with any of the preceding embodiments.

Figure 12A:
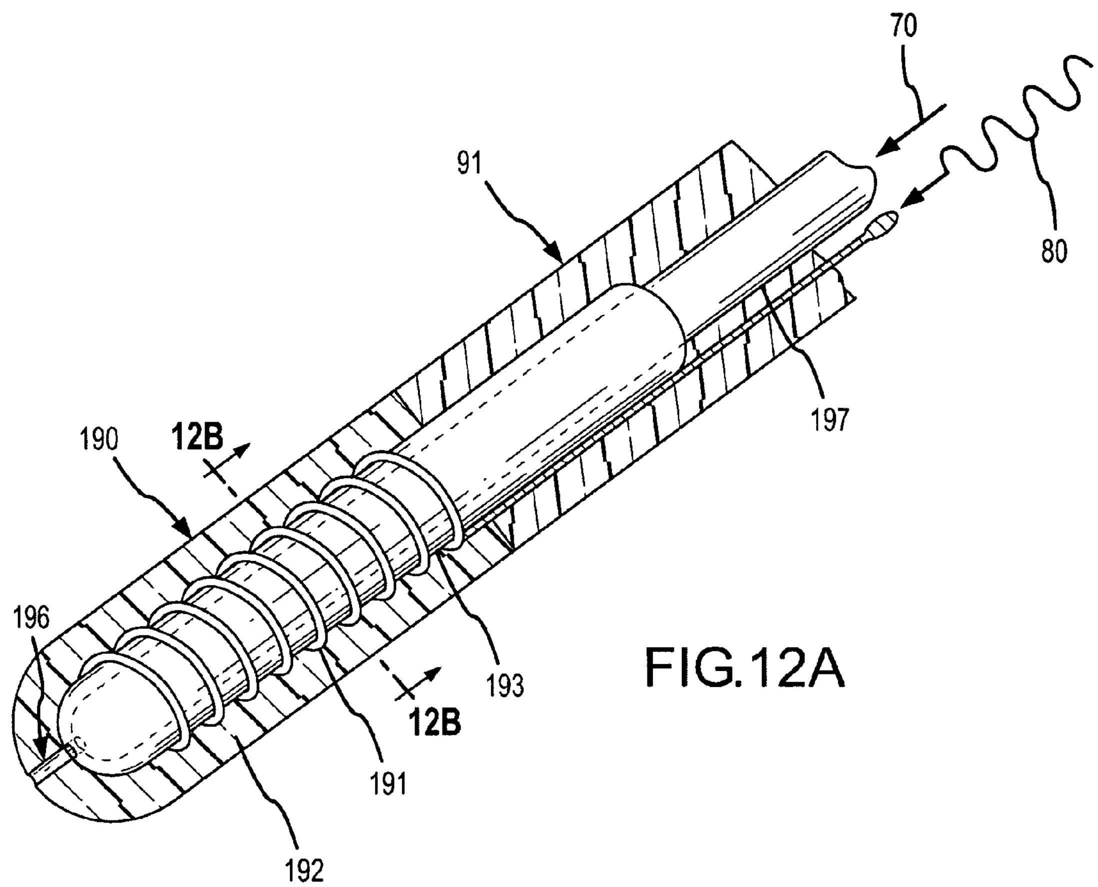
FIGS. 12A and 12B are cross-sectional views of the embodiment of FIG. 6, in which efflux hole 186 has been added.
Figure 12B:
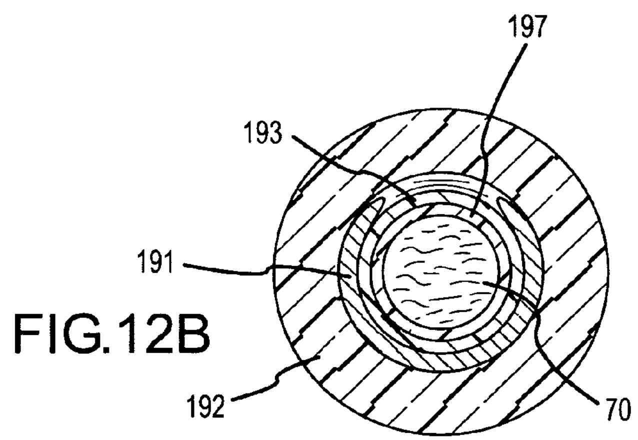

FIGS. 12A and 12B illustrate another preferred embodiment. More particularly, FIGS. 12A and 12B illustrate the embodiment of FIG. 6, in which efflux hole 186 has been added. PSCC electrode 190 extends from a catheter shaft 91 and is connected to an RF energy source (e.g., RF current source 80). PSCC electrode 190 comprises: flexible inner conductive coil 191 in the shape of a helix; an outer PSCC substrate layer 192; a thermally conductive, electrically insulative flexible tube 193 located partially within the helix of the flexible inner conductive coil 191; and a coolant efflux hole 196. Note that a thermally insulative tube 197 is used in at least a portion of the catheter shaft 91 to help reduce the likelihood of cooling fluid 70 (e.g., saline solution) being heated to body temperature. In this embodiment, note that thermally conductive, electrically insulative flexible tube 193 also forms the thermally conductive, electrically insulative, flexible shaft which is present in other embodiments.

Figure 13A:
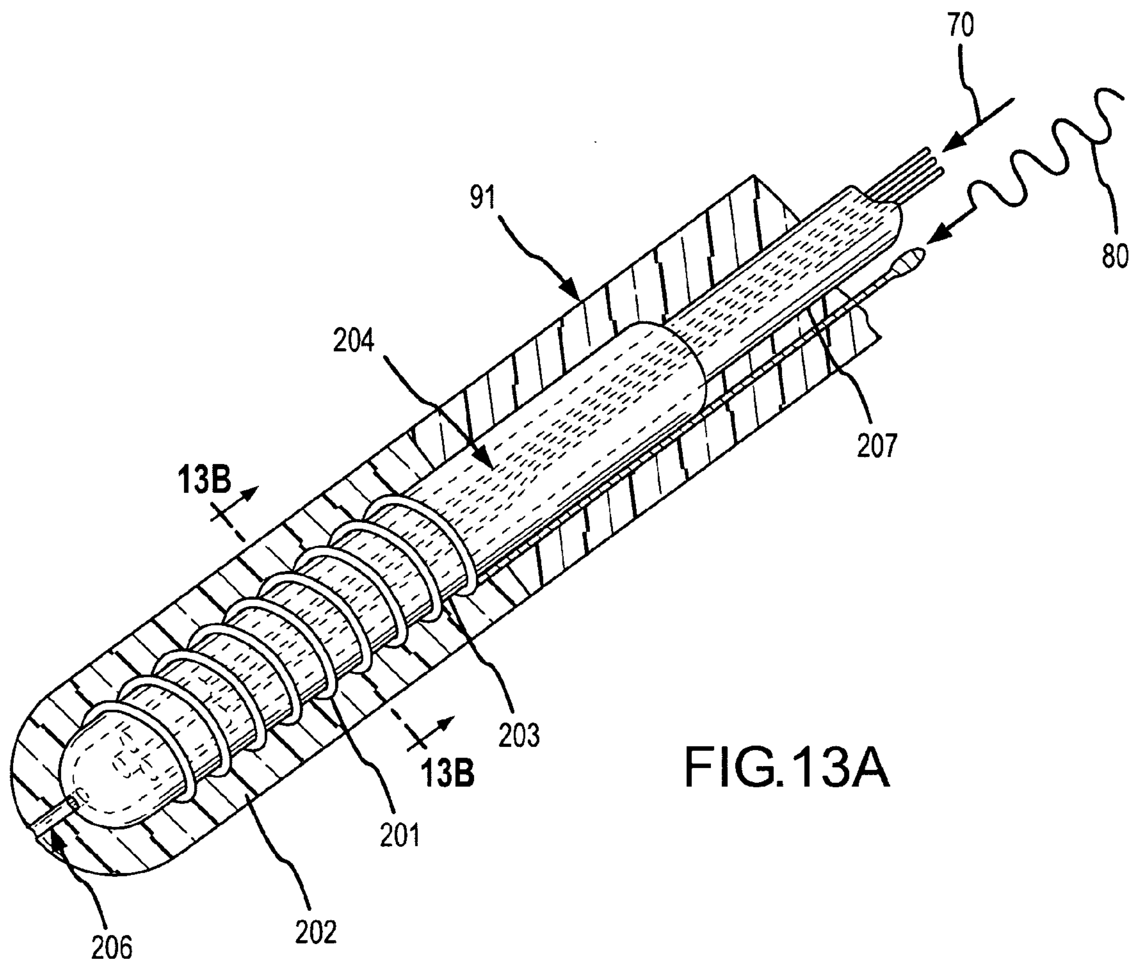
FIGS. 13A and 13B are cross-sectional views of a modified version of the embodiment of FIG. 12A with thermal sensing.
Figure 13B:
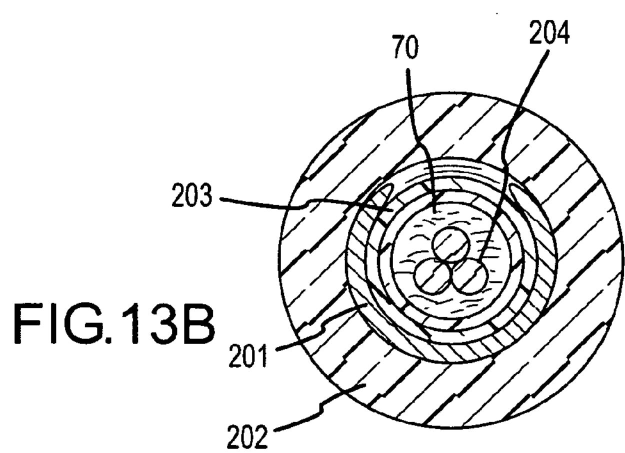

FIGS. 13A and 13B illustrate another preferred embodiment. More particularly, FIGS. 13A and 13B represent a modified version of the embodiment of FIG. 12. PSCC electrode 200 extends from a catheter shaft 91 and is connected to an RF energy source (e.g., RF current source 80). PSCC electrode 200 comprises: flexible inner conductive coil 201 in the shape of a helix; an outer PSCC substrate layer 202; a thermally conductive, electrically insulative flexible tube 203 located partially within the helix of the flexible inner conductive coil 201; a coolant efflux hole 206; and a plurality of thermal sensors 204 located within the thermally conductive, electrically insulative, flexible tube 203 to measure temperatures at various locations therein. Note that a thermally insulative tube 207 is used in at least a portion of the catheter shaft 91 to help reduce the likelihood of cooling fluid 70 being heated to body temperature. In this embodiment, note that thermally conductive, electrically insulative flexible tube 203 also forms the thermally conductive, electrically insulative, flexible shaft which is present in other embodiments.

Figure 14:
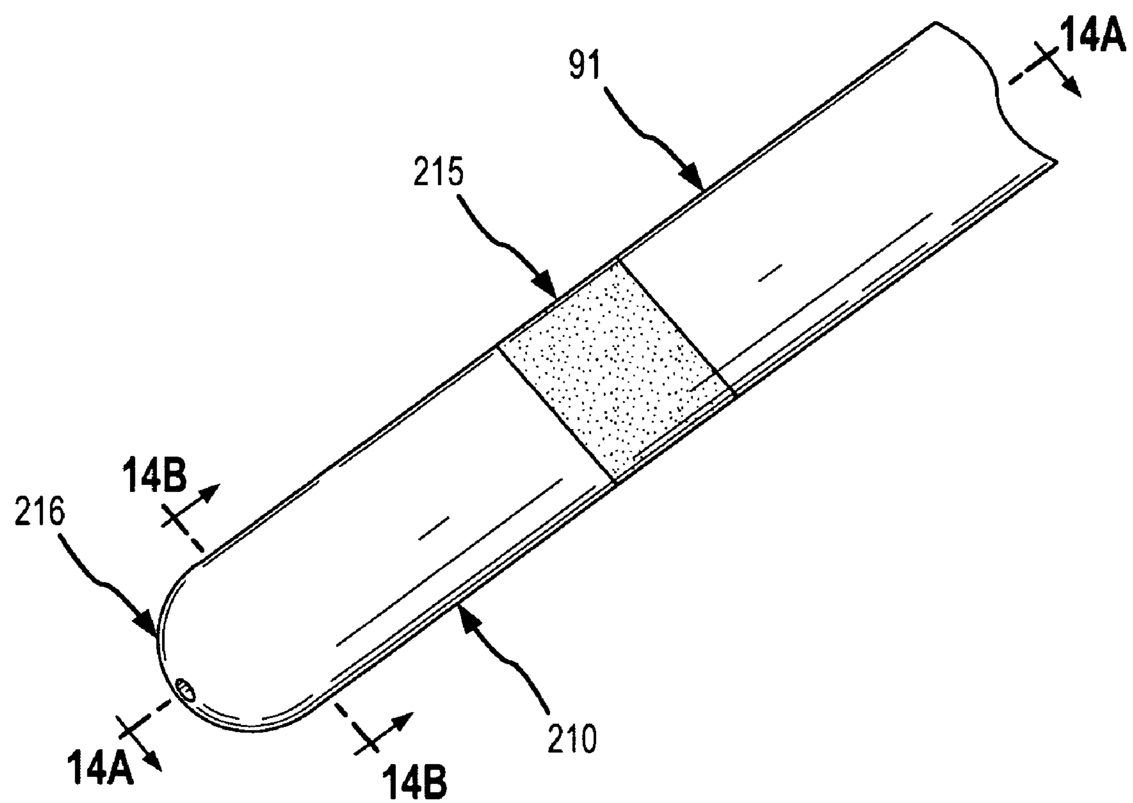
FIG. 14 is a side view of an embodiment that is a modified version of the embodiment of FIG. 11 with a heat sink.

FIG. 14 illustrates yet another preferred embodiment for the invention of the present application. More particularly, FIG. 14 is a modification of the embodiment of FIG. 11. PSCC electrode 210 extends from a catheter shaft 91 and is connected to an RF energy source (not shown). PSCC electrode 210 further comprises a heat sink 215 at the proximal end of the electrode and a coolant efflux hole 216 at the distal end of the electrode.

Figure 15A:
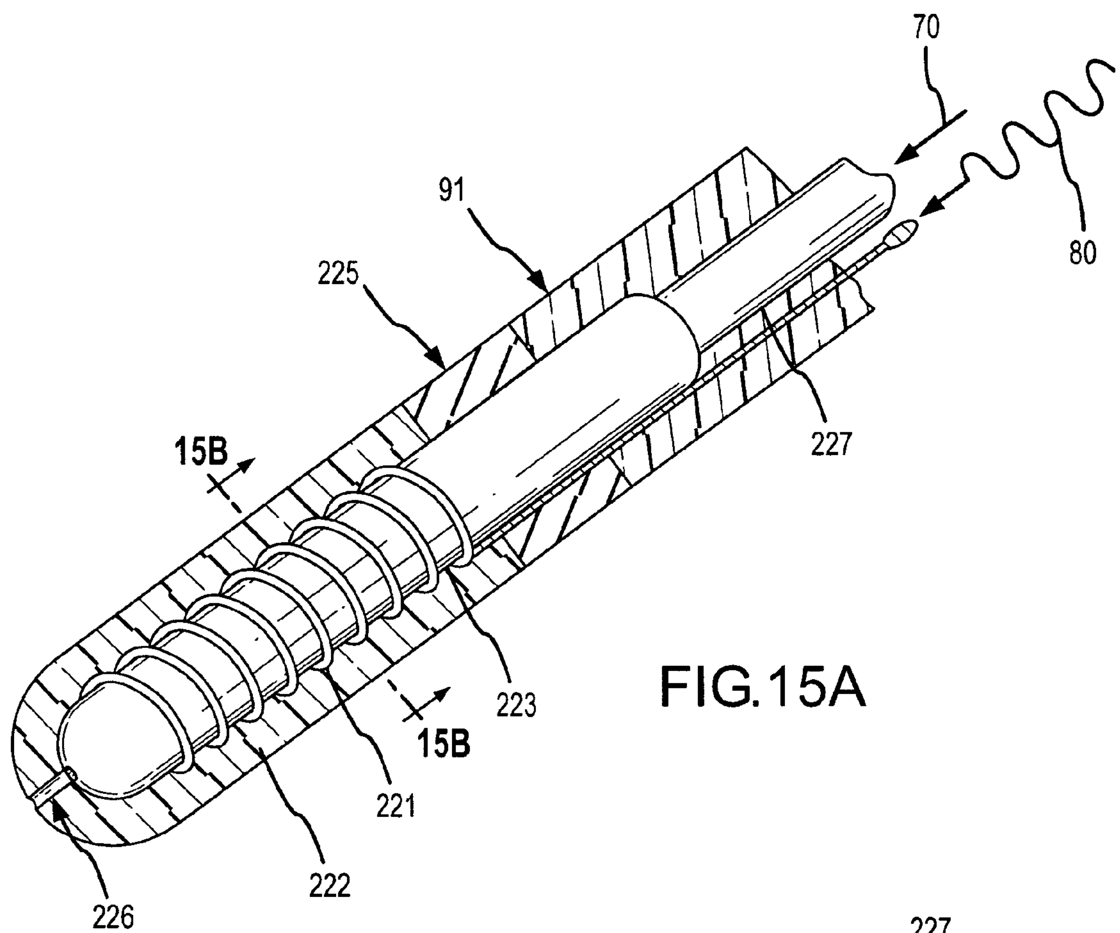
FIGS. 15A and 15B are cross-sectional views of a modification of the embodiment of FIG. 12 with a heat sink.
Figure 15B:
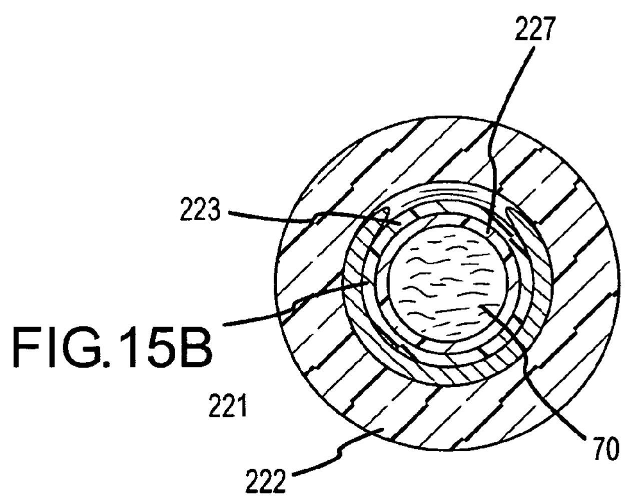

FIGS. 15A and 15B illustrate yet another preferred embodiment. More particularly, FIGS. 15A and 15B represent a modification of the embodiment of FIG. 12. PSCC electrode 220 extends from a catheter shaft 91 and is connected to an RF energy source (e.g., RF current source 80). PSCC electrode 220 comprises: flexible inner conductive coil 221 in the shape of a helix; an outer PSCC substrate layer 222; a thermally conductive, electrically insulative flexible tube 223 located partially within the helix of the flexible inner conductive coil 221; a coolant efflux hole 226; and a heat sink 225 thermally coupled to flexible tube 223. Note that a thermally insulative tube 227 is used in at least a portion of the catheter shaft 91 to help reduce the likelihood of cooling fluid 70 being heated to body temperature. In this embodiment, note that thermally conductive, electrically insulative flexible tube 223 also forms the thermally conductive, electrically insulative, flexible shaft which is present in other embodiments.

Figure 16A:
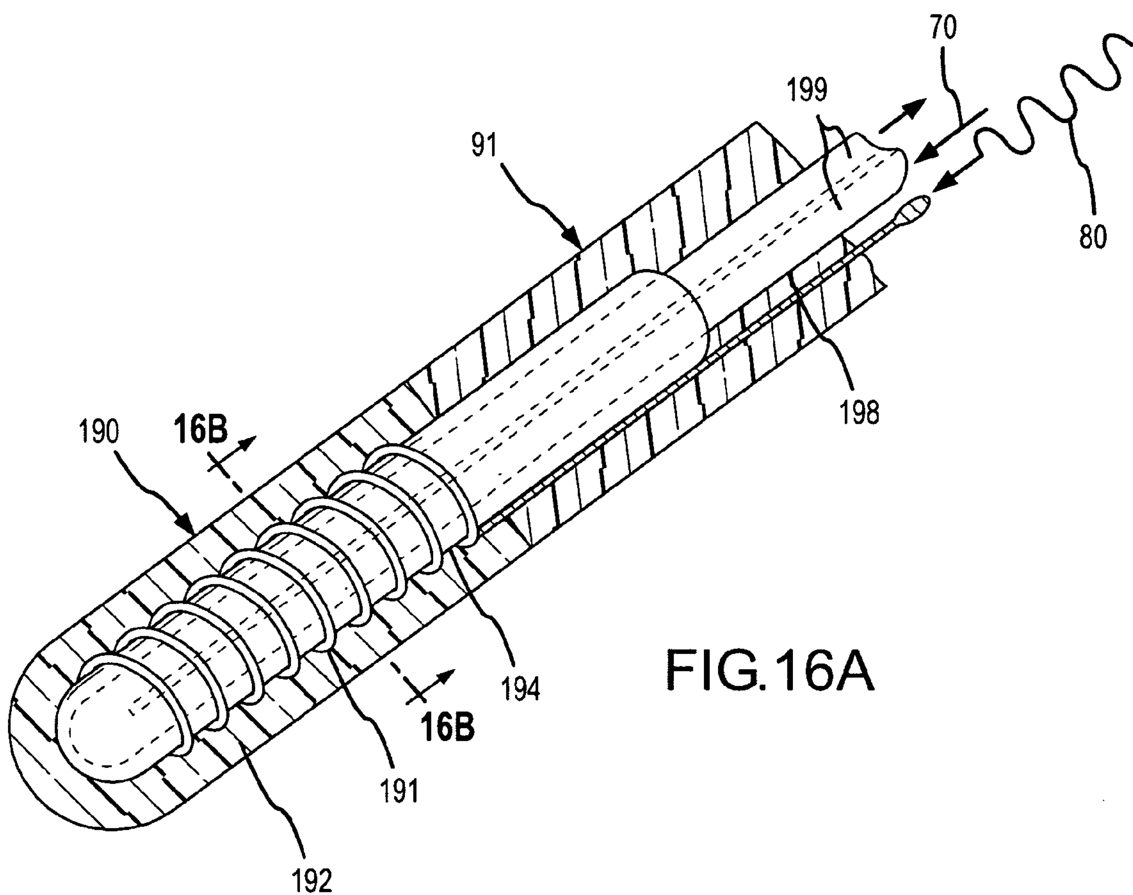
FIGS. 16A and 16B are cross-sectional views of yet another embodiment of the present invention.
Figure 16B:
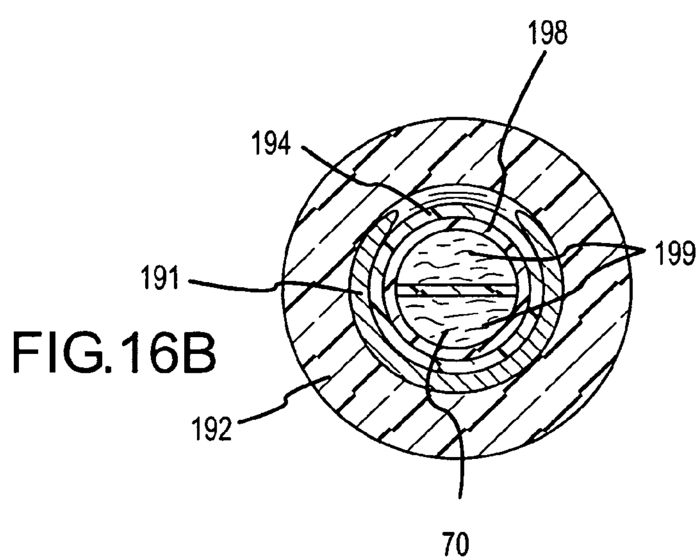

FIGS. 16A and 16B illustrate another preferred embodiment. More particularly, FIGS. 16A and 16B a preferred embodiment, in which a closed loop cooling system has been added. PSCC electrode 190 extends from a catheter shaft 91 and is connected to an RF energy source (e.g., RF current source 80). PSCC electrode 190 comprises: flexible inner conductive coil 191 in the shape of a helix; an outer PSCC substrate layer 192; a thermally conductive flexible shaft 198 located partially within the helix of the flexible inner conductive coil 191; and closed loop cooling passageway 199 located within the flexible shaft 198. Note that a thermally conductive, electrically insulative sleeve 194 may optionally be located between the flexible shaft 198 and inner conductive coil 191. It is contemplated that sleeve 194 may be eliminated, in which case the inner conductive coil 191 may be thermally coupled directly to flexible shaft 198 and closed loop cooling passageway 199. In this embodiment, thermally conductive flexible shaft 198 and closed loop cooling passageway 199 form a closed loop cooling system in which a cooling fluid 70 (e.g., saline) may flow through passage way 199 to cool the distal tip of the catheter during ablation.

In an optional embodiment, any of the electrode designs above may be combined with a processor that monitors the RF current that is being delivered by the RF power source 80. In a preferred embodiment, a computer processor (not shown) will monitor the maximum current being delivered and use this information to help control the ablation process. Because a PSCC's resistance drops monotonically as pressure increases, the amount of current being delivered can be used to assess a degree of contact between the contact surface 100 and tissue 12. Using this information, the computer processor (not shown) may decrease or increase the power level of the RF power source. By way of example only, the computer processor (not shown) may be used to limit the total amount of RF energy that is delivered to a certain tissue area. Depending on the nature of the tissue, the power level may be increased to improve lesion creation.

The PSCC used in the present invention may be chosen to be of a specific sensitivity. For example, highly sensitive PSCCs, which register a sharp change in resistance with a finite amount of applied pressure, may be preferred for soft contact applications such as the atrial wall. Less sensitive PSCCs, which require more pressure to register the same amount of change in resistance, may be preferred for hard contact applications such as ablation in ventricular walls.

The RF source to be used with the present invention is preferably within the radio frequency range of 200-800 kHz, and more preferably with 250 kHz-550 kHz. The source is preferably capable of delivering up to 150 Watts of electrical power.

The embodiments above may be manufactured in a variety of ways. One such method involves forming an electrode assembly as follows. An electrically insulative shaft may be formed using known electrically insulative materials (which may be thermally conductive or thermally insulative). The shaft may be formed of flexible or rigid materials. An electrically conductive element for conducting RF energy may be formed on at least a portion of the electrically insulative shaft. In accordance with the teachings above, the conductive element may be made to be flexible or rigid. A layer of PSCC may be formed over at least a portion of the conductive element, which PSCC material may be compressed under pressure to become electrically coupled with the conductive element. In accordance with the teachings above, the electrode assembly may be optionally coated with one or more conductive layers, which may be either flexible or rigid depending on the application. Preferably, the optional layers are made of a biocompatible, electrically conductive material.

An alternative way to manufacture an electrode assembly of the present invention is as follows. An electrically conductive shaft may be formed using known electrically insulative materials. The shaft may be formed of flexible or rigid materials. A layer of PSCC may be formed over at least a portion of the conductive shaft, which PSCC material may be compressed under pressure to become electrically coupled with the conductive shaft. In accordance with the teachings above, the electrode assembly may be optionally coated with one or more conductive layers, which may be either flexible or rigid depending on the application. Preferably, the optional layers are made of a biocompatible, electrically conductive material.

The electrode assemblies above may be formed a fluid lumen and an efflux hole to permit a cooling fluid to be delivered to the tissue during ablation. The assemblies may also be manufactured to include one or more thermal sensors using techniques that are applicable to other known catheter devices.

It is contemplated that each of the embodiments discussed above may optionally be used in connection with one or more electrically-conductive, outer coverings. Preferably, the outer covering is electrically conductive, such as a flexible wire mesh, a conductive fabric, a conductive polymer layer (which can be porous or nonporous), or a metal coating. The outer covering may be used to not only increase the mechanical integrity, but to enhance the PSCC device's ability to assess the tissue contact (for example, in the when measuring electrical characteristics using a reference electrode connected to the target tissue). In some cases, the outer covering may be made using a biocompatible material in order to help make the overall assembly biocompatible. Preferably the outer covering is flexible, though certain applications may prefer a medium to high degree of rigidity.

Figure 17A:
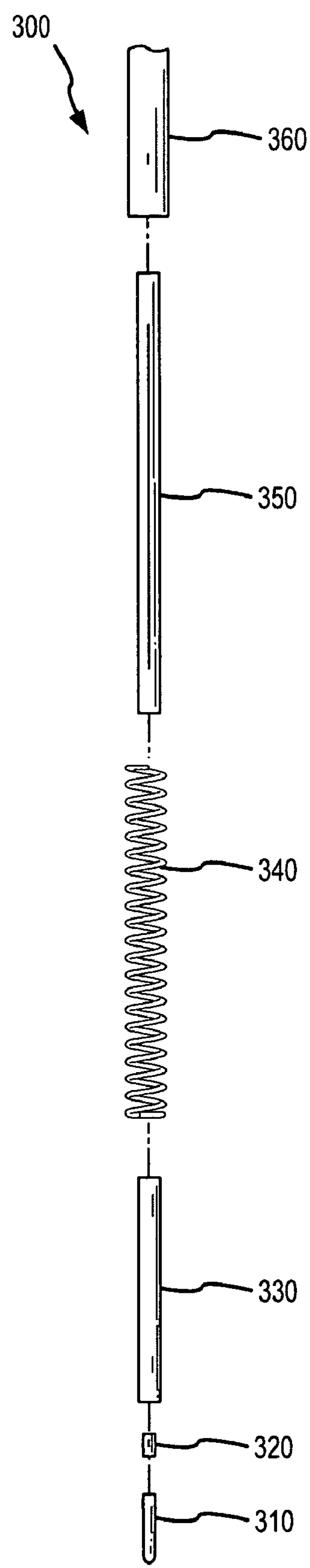
FIGS. 17A, 17B and 17C are side views of another preferred embodiment that utilizes a spring to create a contact sensitive RF ablation assembly.
Figure 17B:
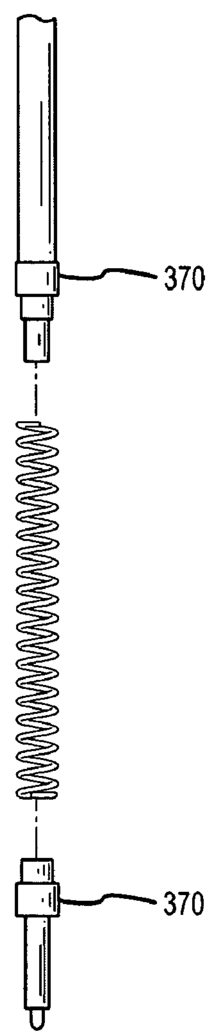
Figure 17C:
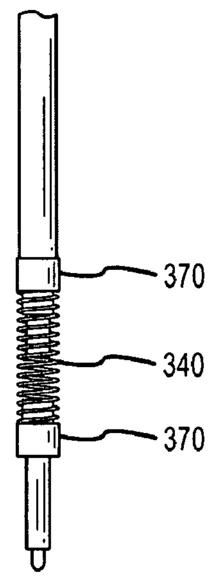

Other novel configurations using pressure sensitive conductive composite materials are possible. FIGS. 17A-17C illustrate one such possibility.

A spring loaded, contact sensitive ablation assembly 300 is depicted in FIGS. 17A-17C. This device is especially useful for dry RF ablation treatments. This embodiment includes: ablation electrode 310; PSCC pill 320; shaft 330; flexible spring 340; conductive pin 350; and shaft 360. Ablation electrode 310 is preferably a 4-8 mm tip, blade or brush. Ablation electrode 310 and PSCC pill 320 may be inserted into shaft 330 with the PSCC pill 320 preferably against the proximal end of electrode 310 in the shaft 330. Shaft 330 may be covered with a heat shrink collar 370, at or near a proximal end of shaft 330. A second heat shrink collar 370 may be placed at the distal end of shaft 360. The heat shrink collars 370 may be used to help anchor the spring 340 for compression support.

Conductive element 350 is preferably designed to deliver ablation energy, such as RF energy to the ablation assembly 300. An external RF power generator may, for example, be coupled to conductive pin 350 to make the conductive pin a power source. Once the conductive pin 350 (preferably made of copper) makes firm contact with the PSCC pill 320, RF power will flow through the PSCC pill 320 to electrode 310, and ultimately be delivered to tissue. When there is no or only nominal pressure applied to electrode 310, the spring 340 will prevent conductive pin 350 from contacting PSCC pill 320, and thus, no energy will be delivered to the tissue. As pressure increases, and sufficient pressure is applied to compress spring 340, conductive pin 350 will make contact with PSCC pill 320, and as pressure continues to increase, PSCC will be compressed with sufficient pressure between conductive pin 350 and electrode 310, such that PSCC pill 320 will become conductive such that RF current will begin to flow. As PSCC pill 320 is compressed further, the impedance of PSCC pill 320 will continue to decrease, and thus, more RF current will pass. One can monitor the impedance and/or the current being delivered and use this information to assess a degree of contact between the electrode 310 and the tissue being treated. For example, as resistance decreases, which results in increases in current, the better contact is obtained. This embodiment also serves as a safety feature. Once you lift the spring-loaded assembly such that it is no longer in compressed contact with a tissue surface, the RF power will automatically shut off. As compression is decreased, the impedance of PSCC pill 320 will increase which decrease the current flow and quickly halt the current flow entirely. Once pressure is decreased to the point that spring 340 no longer maintains compressed contact between conductive pin 350 and PSCC pin 320, the flow is precluded altogether by a gap in contact. This gap provides added assurances that RF current can not be delivered in this uncompressed state. Moreover, the existence of the spring will help to reduce the possibility of arcing during ablation because it effectively breaks the conductive path for current flowing from the electrode to the tissue.

Acceptable materials for ablation electrode 310 include, but are not limited to, stainless steel, nickel titanium (nitinol), tantalum, copper, platinum, iridium, gold, or silver, and combinations thereof. Preferably, the material used to manufacture ablation element 310 is a bio-compatible electrically conductive material, such as platinum, gold, silver, nickel titanium, and combinations thereof.

In a variation of this embodiment, one can compress the spring by pressing down on a knob from the proximal end of the device. Much like how the knob on a retractable pen extends the ball point into a writing position, the knob on this variation will place the conductive pin in conductive contact with the PSCC pill. Preferably, the knob will force the conductive pin to compress down along with the spring and will make firm contact with the PSCC pill, such that the PSCC pill is conductive. More preferably, the amount of RF current may be controlled by the amount of pressure being applied to the knob at the proximal end of the device.

One of ordinary skill will appreciate that while the PSCC materials may be designed to respond to a variety of stresses, the principles and embodiments herein may be adapted to respond to specific stress forces, for example, axial forces, orthogonal forces, twisting, compressing, stretching, etc., without deviating from the scope of the present invention. Furthermore, one of ordinary skill will appreciate that by using springs having different spring constants, additional flexibility can be designed into a spring-loaded PSCC ablation device.

Although multiple embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An electrode assembly comprising:

a conductive pin for conducting ablation energy;

an ablation electrode at a distal end of the electrode assembly; and a pressure sensitive conductive composite element disposed between the conductive pin and the ablation electrode;

said pressure sensitive conductive composite element being positioned such that when it is compressed between the conductive pin and the ablation electrode, the pressure sensitive conductive composite element conducts ablation energy from the conductive pin to the ablation electrode.

2. The electrode assembly of claim 1 further comprising:

a first shaft in which the ablation electrode is disposed at a distal end;

a second shaft in which the conductive pin is disposed; and a spring that permits the first and second shafts to be compressed toward each other.

3. The electrode assembly of claim 2 further comprising:

a collar on each of the first and second shafts such that the spring may be anchored between the two collars during compression.

4. The electrode assembly of claim 2 wherein the pressure sensitive conductive composite element comprises a quantum tunneling composite material.

5. A catheter assembly for conducting ablative energy, said assembly comprising:

a catheter body having an ablation electrode; and a pressure sensitive conductive composite member;

a conductive pin for conducting ablation energy; and a spring that is capable of being in at least a first state and a second state, said first state being one in which the spring electrically decouples the electrode from at least one of the conductive pin and the pressure sensitive conductive composite member; and said spring being compressible into a second state wherein pressure is applied to the pressure sensitive conductive composite member to place it in a conductive state, thereby transferring ablation energy from the conductive pin to the ablation electrode.

6. The catheter assembly of claim 5, wherein the ablation electrode is located on a distal end of the catheter assembly, and wherein the pressure sensitive conductive member is disposed in physical contact with the electrode along the longitudinal axis of the electrode assembly.

7. The catheter assembly of claim 5, further comprising at least one pressure transfer member disposed between the pressure sensitive conductive composite member and the ablation electrode, such that pressure applied to the ablation electrode is transferred through the at least one pressure transfer member to the pressure sensitive conductive composite member.

8. The catheter assembly of claim 5 further comprising:

a collar on each of the first and second shafts such that the spring may be anchored between the two collars during compression.

9. A method of treating tissue, the method comprising:

providing an electrode assembly having: a conductive element for conducting RF energy;

an ablation electrode at a distal end of the electrode assembly; and a pressure sensitive conductive composite member disposed between the conductive element and the ablation electrode;

positioning the electrode assembly in contact with a tissue to be treated;

exerting sufficient force upon the tissue through the electrode assembly such that the pressure sensitive conductive composite member becomes conductive and permits the delivery of RF energy to the tissue.

10. The method of claim 9, wherein at least two of the conductive element, the ablation electrode and the pressure sensitive conductive composite element are electrically decoupled, the method further comprising:

moving at least one of the conductive element, the ablation electrode and the pressure sensitive conductive composite element to electrically couple the conductive pin, the pressure sensitive conductive composite element and the ablation electrode, such that ablation energy may be delivered from the conductive pin to the ablation electrode via the pressure sensitive conductive composite element.

11. The method of claim 9, further comprising:

measuring the resistance along a path of pressure sensitive conductive composite member;

generating a signal that is indicative of the measured resistance having dropped below a set threshold, thereby indicating a desired level of contact between the pressure sensitive conductive composite material and the tissue.

12. The method of claim 9, further comprising:

using a generator to deliver RF energy to the conductive element, said generator having a switch to control delivery of RF energy;

measuring the resistance along a path of pressure sensitive conductive composite member;

generating a signal that is indicative of the measured resistance having dropped below a set threshold;

waiting a predetermined period of time; and controlling the switch of the generator to turn off the RF energy.

13. The method of claim 9, further comprising:

using a generator to deliver RF energy to the conductive element, said generator having a switch to control delivery of RF energy;

monitoring at least one of the generator and the catheter to determine when delivery of RF energy to the tissue has commenced and generating a signal to indicate that delivery of RF energy has commenced;

waiting a predetermined period of time; and controlling the switch of the generator to turn off the RF energy.

14. The method of claim 9, wherein the electrode assembly is being using to ablate tissue without any external fluid being added, and wherein at least two of the conductive element, the ablation electrode and the pressure sensitive conductive composite element are electrically decoupled, the method further comprising:

moving at least one of the conductive element, the ablation electrode and the pressure sensitive conductive composite element to electrically couple the conductive pin, the pressure sensitive conductive composite element and the ablation electrode, such that ablation energy may be delivered slowly via the pressure sensitive conductive composite element so as to mitigate the effects of arcing.

15. An electrode assembly comprising:

a conductive pin for conducting ablation energy;

an ablation electrode at a distal end of the electrode assembly;

a pressure sensitive conductive composite element disposed between the conductive pin and the ablation electrode; and an engagement assembly that moves at least one of the conductive pin, the pressure sensitive conductive composite element and the ablation electrode to create an engagement position and a non-engagement position, wherein the engagement position electrically couples the conductive pin, the pressure sensitive conductive composite element and the ablation electrode, such that ablation energy may be delivered from the conductive pin to the ablation electrode via the pressure sensitive conductive composite element; and wherein the non-engagement position electrically decouples at least two of the conductive pin, the pressure sensitive conductive composite element, and the ablation electrode, such that ablation energy is not delivered to the ablation electrode.

16. The electrode assembly of claim 15 wherein the engagement assembly comprises:

a first shaft in which the ablation electrode is disposed at a distal end;

a second shaft in which the conductive pin is disposed; and a spring that permits the first and second shafts to be compressed toward each other.

17. The electrode assembly of claim 16 further comprising:

an anchor on each of the first and second shafts such that the spring is secured between the two anchors during compression.

18. The electrode assembly of claim 16 wherein the pressure sensitive conductive composite element comprises a quantum tunneling composite material.

* * * * *